United States Patent [19]

Austin et al.

[11] Patent Number: 5,427,663

[45] Date of Patent: Jun. 27, 1995

[54] MICROLITHOGRAPHIC ARRAY FOR MACROMOLECULE AND CELL FRACTIONATION

[75] Inventors: Robert H. Austin, Princeton, N.J.; Wayne D. Volkmuth, Menlo Park, Calif.; Lynn C. Rathburn, Ithaca, N.Y.

[73] Assignees: British Technology Group USA Inc., Gulph Mills, Pa.; Cornell Research Foundation, Inc., Ithaca, N.Y.

[21] Appl. No.: 74,432

[22] Filed: Jun. 8, 1993

[51] Int. Cl.[6] .................. G01N 27/26; G01N 27/447; B03B 5/00
[52] U.S. Cl. ............................ 204/180.1; 204/299 R; 209/127.1; 209/155; 209/156
[58] Field of Search ............ 204/299 R, 182.8, 188.1; 209/127.1, 131, 155, 156

[56] References Cited

U.S. PATENT DOCUMENTS 4,561,157  12/1985  Lowe et al. ........................... 29/898

FOREIGN PATENT DOCUMENTS

| 4152885 | 5/1992 | Japan . |
| 2238619 | 6/1991 | United Kingdom . |
| 2239311 | 6/1991 | United Kingdom . |
| WO91/11262 | 8/1991 | WIPO . |
| WO91/13338 | 9/1991 | WIPO . |

OTHER PUBLICATIONS

Abstract of Japanese Patent No. 4,152,885 dated May 26, 1992.
Abstract of Great Britain Patent No. 2,239,311 dated Jun. 26, 1991.
"Micromechanics Imitate Blood Vessels", Design News 15 (Mar. 22, 1993).
Mark Ivker, "Direct Observation of Reptation in Artificial Gel Environments" (Spring, 1991) (Bachelor of Arts Thesis, Princeton University).
George Wallis et al., "Field Assisted Glass-Metal Sealing", 40 J. Applied Physics 3946-49 (Sep., 1969).
Masao Washizu, et al., "Handling Biological Cells Utilizing a Fluid Integrated Circuit", 26 IEEE Transactions on Industry Applications 352-357 (1990).
Masao Washizu, et al., "Handling Biological Cells Utilizing a Fluid Integrated Circuit", IEEE Industry Applications Society Annual Meeting Presentations I73-5-40 (Oct. 2-7, 1988).
W. D. Volkmuth et al., "DNA Electrophoresis in Microlithographic Arrays", 356 Nature 600-02 (Aug. 13, 1992).
W. Volkmuth et al., "Observation of Electrophoresis of Single DNA Molecules in Nanofabricated Arrays", presentation at joint annual meeting of Biophysical Society and the American Society for Biochemistry and Molecular Biology (Feb. 9-13, 1992).

*Primary Examiner*—John Niebling
*Assistant Examiner*—John S. Starsiak, Jr.
*Attorney, Agent, or Firm*—Workman Nydegger & Seeley

[57] ABSTRACT

A sorting apparatus and method for fractionating and simultaneously viewing individual microstructures, such as free cells, viruses, macromolecules, or minute particles in a fluid medium. The sorting apparatus is composed of a substrate having a receptacle located therein, the receptacle having sidewalls and a floor. An array of obstacles is positioned within the receptacle with the obstacles upstanding from the floor of the receptacle. A transparent cover overlies the array of obstacles to cover the receptacle and afford visual observation of migration of the microstructures exclusively through the array of obstacles. Electrodes may be positioned within the receptacle to generate an electric field in the fluid medium in the receptacle in order to induce the migration of the microstructures. Migration of the microstructures may also occur, for example, by a hydrodynamic field, an optical field, a magnetic field, or a gravity field applied to the receptacle. The obstacles of the array of obstacles may be of various shapes such as round posts, rectangular bunkers, or v-shaped or cup-shaped structures. The arrays of obstacles are formed of a predetermined and reproducible pattern, and can be reused. Methods for manufacturing and using the apparatus are also claimed.

75 Claims, 12 Drawing Sheets

MICROLITHOGRAPHIC ARRAY FOR MACROMOLECULE AND CELL FRACTIONATION

BACKGROUND

1. The Field of the Invention

The invention relates to apparatus and methods for fractionating microstructures such as free cells, viruses, macromolecules, or minute particles. More particularly, the present invention relates to apparatus and methods for sorting such microstructures in suspension in a fluid medium while simultaneously viewing individual of those microstructures during the process.

2. Background Art

The sizing, separation, and study of microstructures such as free cells, viruses, macromolecules, and minute particles are important tools in molecular biology. For example, this fractionation process when applied to DNA molecules is useful in the study of genes and ultimately in planning and the implementation of genetic engineering processes. The fractionation of larger microstructures, such as mammalian cells, promises to afford cell biologists new insights into the functioning of these basic building blocks of living creatures.

A. Macromolecule Fractionation

While many types of macromolecules may be fractionated by the apparatus of the present invention, the fractionation of a DNA molecule will be discussed below in detail as one example.

The DNA molecules in a single cell of a complex organism contain all of the information required to replicate that cell and the organism of which it is a part. A DNA molecule is a double helical chain of four different subunits that occur in a genetically coded succession along the chain. The four subunits are the nitrogenous bases, adenine, cytosine, guanine, and thymine. The size of such a molecule is measured by the number of such bases it contains. Natural DNA molecules range in size from a few kilobasepairs in length to hundreds of megabasepairs in length. The size of a DNA molecule is roughly proportional to the number of genes the molecule contains.

The size of a DNA molecule can also be expressed by its molecular weight, its length, or the number of basepairs it includes. If the number of basepairs is known, that number can be converted into both the length and the molecular weight of the DNA molecule. One method for estimating the size of small DNA molecules is the process of gel electrophoresis.

In gel electrophoresis an agarose gel is spread in a thin layer and allowed to harden into a firm composition. The composition comprises a fine network of fibers retaining therewithin a liquid medium, such as water. The fibers of the agarose gel cross and interact with each other to form a lattice of pores through which molecules smaller than the pores may migrate in the liquid retained in the composition. The size of the pores in the lattice is determined generally by the concentration of the gel used.

Slots are cast in one end of the gel after the gel is hardened, and DNA molecules are placed into the slots. A weak electric field of typically 1-10 volts per centimeter is then generated in the gel by placing the positive pole of an electric power source in one end of the gel and the negative pole of the power source in the opposite end. In DNA electrophoresis, the negative pole of the power source is placed in the gel at the end of the composition in which the slots containing the DNA are located. The DNA molecules, being negatively charged, are induced by the electric field to migrate through the gel to the positive pole of the power source at the other end of the composition. This occurs at speeds of typically only a few centimeters per hour.

The electrophoretic mobility of the molecules can be quantified. The electrophoretic mobility of a molecule is the ratio of the velocity of the molecule to the intensity of the applied electric field. In a free solution, the mobility of a DNA molecule is independent of the length of the molecule or of the size of the applied electric field. In a hindered environment, however, aside from the structure of the hindered environment, the mobility of a molecule becomes a function of the length of the molecule and the intensity of the electric field.

The gels used in gel electrophoresis is just such a hindered environment. Molecules are hindered in their migration through the liquid medium in the gel by the lattice structure formed of the fibers in the gel. The molecules nevertheless when induced by the electric field, move through the gel by migrating through the pores of the lattice structure. Smaller molecules are able to pass through the pores more easily and thus more quickly than are larger molecules. Thus, smaller molecules advance a greater distance through the gel composition in a given amount of time than do larger molecules. The smaller molecules thereby become separated from the larger molecules in the process. In this manner DNA fractionation occurs.

While gel electrophoresis is a well known and often used process for DNA fractionation, electrophoretic mobility is not well understood in gel lattice structures. Thus, the process has several inherent limitations. For example, the pore size in the lattice of gels cannot be accurately measured or depicted. Therefore, the lengths of the molecules migrating through the lattice cannot be accurately measured. It has also been found that DNA molecules larger than 20 megabasepairs in length cannot be accurately fractionated in gels. Apparently, the pore size in the lattice of such materials cannot be increased to permit the fractionation of larger molecules, much less even larger particles, viruses, or free cells.

Further, the lattice structure formed when a gel hardens is not predictable. It is not possible to predict the configuration into which the lattice structure will form or how the pores therein will be positioned, sized, or shaped. The resulting lattice structure is different each time the process is carried out. Therefore, controls and the critical scientific criteria of repeatability cannot be established.

Gel electrophoresis experiments cannot be exactly duplicated in order to predictably repeat previous data. Even if the exact lattice structures formed in one experiment were determinable, the structure could still not be reproduced. Each experiment is different, and the scientific method is seriously slowed.

Also, the lattice structure of a gel is limited to whatever the gel will naturally produce. The general size of the pores can be dictated to a degree by varying the concentration of the gel, but the positioning of the pores and the overall lattice structure cannot be determined or designed. Distinctive lattice structures tailored to specific purposes cannot be created in a gel.

Further, because the lattice structure arrived at depends upon the conditions under which hardening of the gel occurs, the lattice structure even in a single composition need not be uniform throughout.

Another shortcoming of gel electrophoresis is caused by the fact that a gel can only be disposed in a layer that is relatively thick compared to the pores in its lattice structure, or correspondingly to the size of the DNA molecules to be fractionated. Thus, the DNA molecules pass through a gel in several superimposed and intertwined layers. Individual DNA molecules cannot be observed separately from the entire group. Even the most thinly spread gel is too thick to allow an individual DNA molecule moving through the gel to be spatially tracked or isolated from the group of DNA molecules.

Once a gel has been used in one experiment, the gel is contaminated and cannot be used again. The gel interacts with the materials actually used in each experiment, and cleaning of the gel for later reuse is not possible. A gel layer must therefore be disposed after only one use. This also frustrates the scientific objective of repeatability.

Finally, simple gel electrophoresis cannot be used to fractionate DNA molecules larger than approximately 20 kilobases in length. To overcome this fact, it is known to pulse the applied electric field to attempt to fractionate longer DNA molecules. This technique, however, results in extremely low mobility and requires days of running time to achieve significant fractionation. Also, the numerical predictions of the theories developed to explain the results of this technique depend critically on the poorly known pore size and distribution in the lattice of the gel.

B. Cell Fractionation

The flexibility of cells is a structural variable of some interest to cell biologists. The flexibility of cells and the effects of various environments on cell flexibility is important to the study of the aging process in cells. However, cell fractionation based upon cell flexibility is not easily accomplished in the prior art.

For example, various cells have round or oval shapes with various diameters. The shapes are often determined by an underlying cytoskeleton.

When the cells are circulating in the human body, the cells must, on several occasions, pass through variously sized openings and passageways. This requires substantial flexibility of the cell. The inability to pass through these openings can be caused by the aging of a cell, reactions to specific chemical environments, and other metabolic changes. When referring to red blood cells, poor red blood cell flexibility results in serious consequences for the larger organism. With respect to cells such as cancer cells, poor flexibility may result in growth and spread of tumors.

Cancer cells are generally thought to settle in the human body in blood vessels larger than the cells themselves and stick to those vessels through a special adhesion molecule. As the cancer cells stick to the vessels, new tumors begin to grow. New information, however, has indicated that the cancer cells move too quickly to become adhered to the vessels in this fashion. It is now thought that cells may start new tumors when they become stuck in vessels too narrow for the cancer cells to pass through. The flexibility of the cancer cells is important in determining the deleterious effect of the cell.

Three physical limitations impinge on the flexibility of many cells. First, many cells must maintain both a constant volume V and a constant surface area A as it deforms. Second, the cell membrane, while very flexible, cannot increase in area. It will tear, if forced to do so. Third, as a cell ages it loses membrane and the surface-to-volume ratio decreases.

For example, a biconcave red blood cell has a maximum diameter of about 8 microns, a surface area of about 140 microns square, and a volume of about 95 microns cube in the normal state. It can be shown that for mature red blood cells for openings smaller in diameter than approximately 3 microns, the constraints of constant volume V and surface area A cannot be met. The passage of a red blood cell through a passageway of that size, thus, cannot occur without membrane rupture. Since the smallest capillary openings are but approximately 3.5 microns, red blood cells passing through the capillary bed are uncomfortably close to being ruptured. Accordingly, small changes in the physical variables that control deformability can lead to microangiopathy and severe organism distress.

There exist several techniques for measuring cell flexibility and deformability. These range from the elegant and pioneering micropipette aspiration techniques, to the nucleopore filtration and laminar stress elongation techniques. The latter are termed ektacytometry. All are very useful and have provided an excellent initial database for studying red blood cell deformation, but each has certain weaknesses.

The micropipette aspiration technique can only study one cell at a time. The nucleopore filtration technique does not allow observation of cells during the actual passage thereof through openings. Ektacytometry does not deform cells in narrow passages.

OBJECTS AND SUMMARY OF THE INVENTION

It is accordingly a broad objective of the present invention to provide an improved method and apparatus for fractionating microstructures, such as macromolecules, viruses, free cells, and minute particles.

Another object of the present invention is to facilitate research into the behavior and structure of macromolecules, such as DNA molecules, proteins and polymers.

Correspondingly it is an object of the present invention to enhance the effectiveness of electrophoresis techniques currently applied to the fractionation of such macromolecules.

Yet another object of the present invention is to permit fractionation of DNA molecules in excess of 20 megabasepairs in length, without resorting to the use of a pulsed electric field.

Yet another object of the present invention is to provide a hindered environment in which to conduct macromolecular electrophoresis, wherein the lattice structure of the hindered environment can be designed at will and replicated with repeatable consistency.

Another object of the present invention is to provide such a lattice structure in which the distribution, size, and shape of the pore therein are substantially uniform.

Yet another object of the present invention is to provide an apparatus for fractionating macromolecules while simultaneously observing individual of the macromolecules during the process.

Yet another object of the present invention is to advance the study of the structure and mechanics of free cells, such as red blood cells, cancer cells, and $E.\ coli$ cells.

It is yet another object of the present invention to provide an apparatus for fractionating cells according to the elasticity thereof and other physical properties which are otherwise difficult to probe by biological markers.

In particular, it is an object of the present invention to provide a method and apparatus for observing cell behavior during the passage of cells through channels in essentially a single layer in single file.

Yet another object of the present invention is to provide an apparatus for sorting and viewing microstructures, which is not contaminated by the microstructures being sorted.

Yet another object of the present invention is to increase the mobility of large molecules during electrophoresis.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein, a sorting apparatus is provided for fractionating and simultaneously viewing individual microstructures such as free cells, viruses, macromolecules, or minute particles in a fluid medium. The sorting apparatus allows the microstructures to be observed in essentially a single layer and whereby a particular microstructure can be tracked throughout. One embodiment of an apparatus incorporating the teachings of the present invention comprises a substrate having a shallow receptacle located on a side thereof. The receptacle has first and second ends and a floor bounded on opposite sides by a pair of upstanding opposed side walls extending between the first and second ends of the receptacle. Migration of the microstructures from the first end of the receptacle to the second end of the receptacle defines a migration direction for the receptacle. The height of the side walls defines a depth of the receptacle. The depth is commensurate with the size of the microstructures in the fluid medium, whereby the microstructures will migrate in the fluid through the receptacle in essentially a single layer.

According to one aspect of the present invention, the array further comprises sifting means positioned within the receptacle intermediate the first and second ends traversing the migration direction. The sifting means are for interacting with the microstructures to partially hinder migration of the microstructures in the migration direction in the fluid medium.

In one embodiment of such a sifting means, an array of obstacles is provided upstanding from the floor of the receptacle. The array of obstacles is arranged in a predetermined and reproducible pattern. The obstacles may comprise posts, bunkers, v-shaped and cup-shaped structures, and other shapes of structures. In a preferred embodiment, the receptacle and array of obstacles therein are simultaneously formed on a side of the substrate using microlithography techniques.

According to another aspect of the present invention, the apparatus further comprises ceiling means positioned over the sifting means for covering the receptacle and for causing migration of the microstructures in essentially a single layer through the sifting means exclusively. The ceiling means are so secured to the sifting means as to preclude migration of microstructures between the sifting means and the ceiling means. In one embodiment of an apparatus incorporating the teachings of the present invention, such a ceiling means comprises a coverslip which extends across the substrate from one of the pair of upstanding opposing side walls to the other of the pair of upstanding opposed side walls with the tops of the obstacles in the array bonded to the adjacent side of the coverslip. Optimally, the coverslip and the substrate have similar thermal coefficients of expansion. Also, preferably the substrate and the array of obstacles are comprised of a material that is noninteractive in a normal range of temperatures with the microstructures to be fractionated therein.

Optionally, the coverslip may be transparent, thereby to afford for visual observation of the microstructures during sorting. The transparent form of the coverslip represents one example of a structure capable of performing the function of what will hereinafter be referred to as a "capping means" for the present invention.

In another aspect of an apparatus incorporating the teachings of the present invention, the array includes electric force means for generating in the receptacle an electric field used to induce charged microstructures to migrate through the fluid medium from one end of the receptacle to the other. In one embodiment, such an electric force means may comprise a first electrode positioned at the first end of the receptacle and a second electrode positioned at the second end of the receptacle. The electrodes may comprise metal strips disposed on the floor of the receptacle. A power source is electrically coupled between the first and second electrodes.

In yet another aspect of the present invention, an apparatus incorporating the teachings thereof further comprises sensor means positioned within the array of obstacles for sensing the intensity of the electric field generated within the array. The sensor means may optionally be electrically coupled with the electric force means to vary the intensity of the electric field in a predetermined manner. In one embodiment of the sensor means, first and second sensor electrodes are positioned within the array of obstacles, and control means are coupled to the first and second electrodes for maintaining the electric field in the array at a predetermined intensity.

In one embodiment of the present invention, such a control means includes a differential amplifier circuit having first and second input terminals coupled respectively to the first and second sensor electrodes. The differential amplifier circuit produces an output signal corresponding to the intensity of the electric field in the array between the first and second sensor electrodes. Comparator means are coupled to the differential amplifier for producing a control signal reflecting the difference between the output signal of the differential amplifier and a reference voltage reflecting the predetermined intensity of the electric field in the array. Driver means are coupled to the comparator means for varying the intensity of the electric field in accordance with the control signal produced by the comparator means.

The present invention also contemplates a method for manufacturing an apparatus as described above. In the method a receptacle is formed on one side of a substrate having a floor bounded by a pair of upstanding opposing side walls. An array of obstacles are built within the receptacle. Preferably the step of forming the receptacle and the step of building the array are performed simultaneously. To do so, a photoresist layer is positioned over areas of the substrate intended to correspond to the tops of the obstacles of the arrays. Then the substrate is etched to a predetermined depth equal to the depth of the receptacle. The receptacle with the array of obstacles upstanding therein is formed as a result. The photoresist layer is then dissolved from the substrate.

Ultimately the method of the present invention includes the step of securing a transparent coverslip to the top of each of the obstacles. To do so the coverslip is positioned over the array of obstacles in contact with the top of each. An electric field is applied between the coverslip and the array of obstacles.

The present invention also contemplates a method for sorting and simultaneously viewing individual microstructures. In that method the microstructures are placed in a fluid medium and introduced into one end of an apparatus as described above. The microstructures are then induced to migrate in the fluid through the array of obstacles and visually observed during the process.

An additional embodiment within the scope of the present invention comprises an apparatus for sorting and simultaneously viewing cells in a fluid medium in order to study flexibility of cells and the effects of various environment on cells. The apparatus comprises a substrate having a shallow receptacle located on a side thereof and channeling means positioned within the receptacle for allowing passage of cells through the receptacle in essentially a single layer and in single file. In one embodiment of the present invention, such a channeling means comprises passageways positioned within the receptacle through which the cells may pass.

The apparatus can be used to measure the amount of energy consumed during movement of the cells.

BRIEF DESCRIPTION OF THE DRAWINGS

In order to understand the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered limiting of its scope, the invention will be described and explained with additional specificity and detail through the use of the accompanying drawings in which.

DETAILED DESCRIPTION OF THE PREFERRED EMBODIMENTS

The present invention provides a method and apparatus that facilitates the fractionation of many types of microstructures. For example, the present invention allows successful fractionation of extremely long DNA molecules of chromosomal length in low quantities, such as even single molecules. The present invention also facilitates the fractionation of much larger microstructures, such as red blood cells.

Each application will be described in turn below.

A. Macromolecule Fractionation

Although reference will be made herein to the fractionation of DNA molecules, it should be noted that fractionation of other macromolecules and microstructures, such as proteins, polymers, viruses, cells, and minute particles, is considered to be within the scope of the present invention.

The diffusion of long polymers in complex environments where the mobility of the polymer is greatly perturbed is both a challenging statistical physics problem and a problem of great importance in the biological sciences. The length fractionation of charged polymers, such as DNA in gels, is a primary tool of molecular biology. One of the main stumbling blocks to understanding quantitatively the physical principles behind the length-dependent mobility of long polymers in complex environments has, however, been the ill-characterized nature of the hindering environment, the gel. It is possible, however, using the present invention to generate complex environments which are very well characterized and consistently reproducible.

Figure 1:
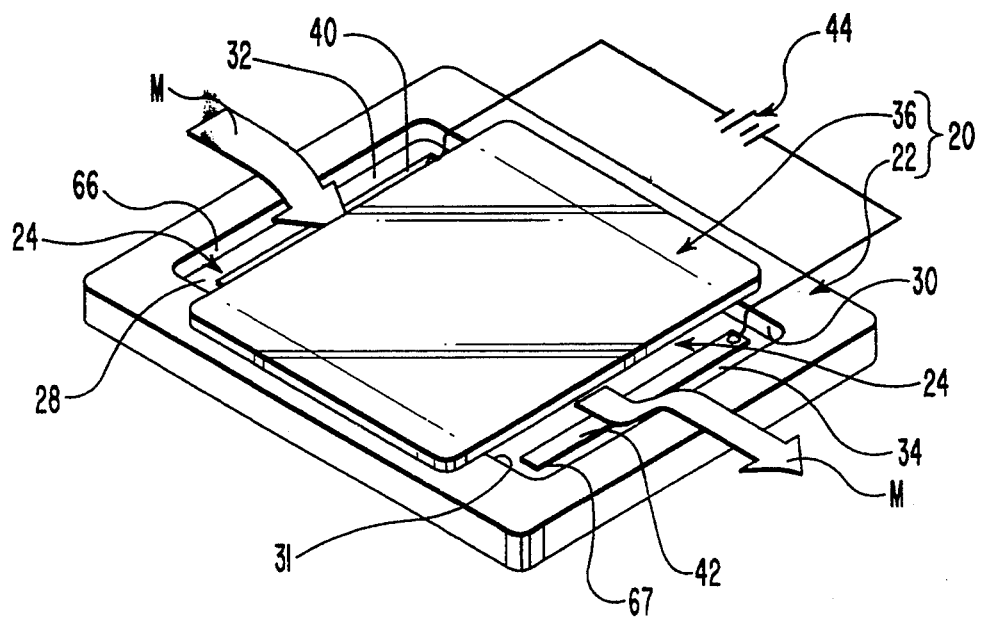
FIG. 1 is a perspective view of one embodiment of a sorting apparatus incorporating the teachings of the present invention.

Referring to FIG. 1, a sorting apparatus 20 is illustrated for fractionating and simultaneously viewing microstructures such as free cells, macromolecules, and minute particles in a fluid medium in essentially a single layer. Sorting apparatus 20 is comprised of a substrate 22 having a shallow receptacle 24 located on a side 26 thereof. In the embodiment shown, receptacle 24 is recessed in side 26 of substrate 22, although other structures for producing a recess such as receptacle 24 would be workable in the context of the present invention.

Figure 2:
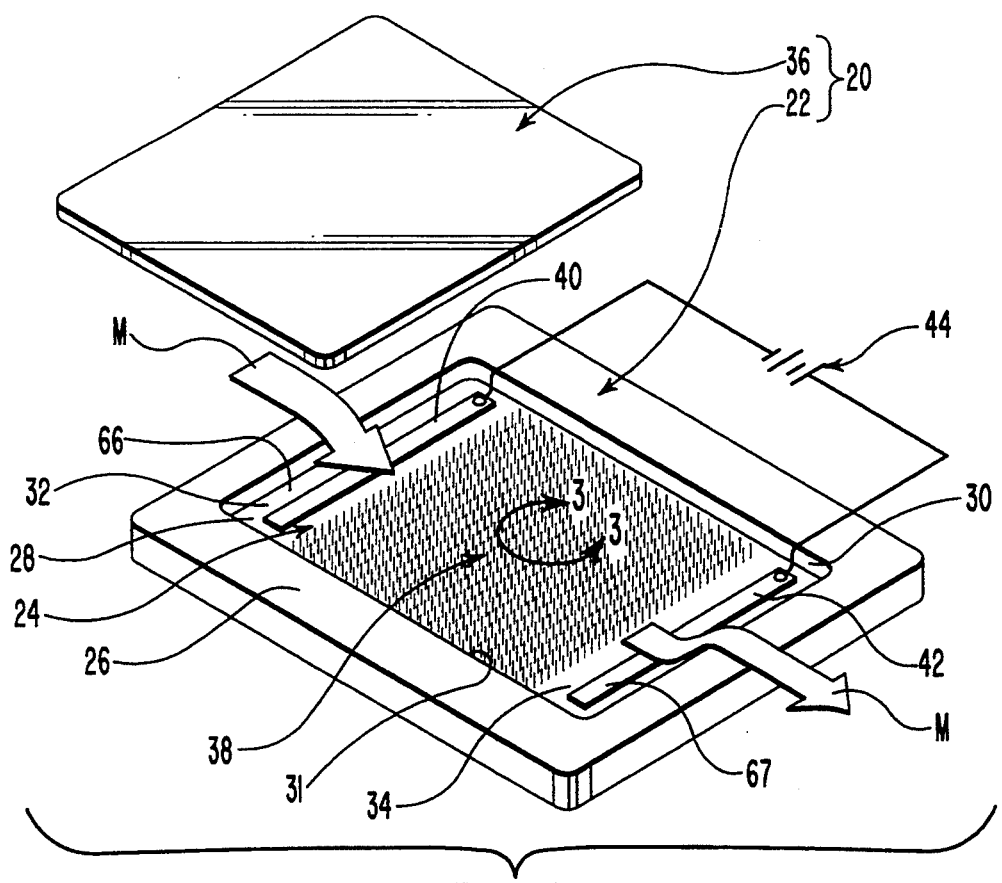
FIG. 2 is an exploded view of the apparatus illustrated in FIG. 1 with the transparent coverslip thereof shown separated from the substrate to more fully reveal an array of obstacles therebetween.

Receptacle 24 includes a floor 28 shown to better advantage in FIG. 2 bounded by a pair of upstanding opposing side walls 30, 31 and a first end 32 and a second end 34. The height of side walls 30, 31 define a depth of receptacle 24. The depth of receptacle 24 is commensurate with the size of the microstructures to be sorted in sorting apparatus 20. The depth of receptacle 24 is specifically tailored to cause those microstructures in a fluid medium in receptacle 24 to form essentially a single layer. Thus, when the microstructures are caused to migrate in the fluid medium through receptacle 24, the microstructures do so in essentially the single layer. The migration of the microstructures occurs in a migration direction indicated by arrow M defined relative to sorting apparatus 20.

Substrate 22 may be comprised of any type material which can be photolithographically processed. Silicon is preferred, however other materials, such as quartz and sapphire can also be used.

In accordance with one aspect of the present invention, ceiling means are provided for covering receptacle 24 intermediate first end 32 and second end 34 thereof and for causing the migration of the microstructures within receptacle 24 to occur in essentially a single layer. As shown by way of example and not limitation, in FIG. 1, a coverslip 36 extends across receptacle 24 in substrate 22 from one of the pair of upstanding opposing side walls 30 to the other of said pair of upstanding opposing side walls 31. The manner by which coverslip 36 is bonded to side 26 of substrate 22 will be discussed in detail subsequently.

According to one aspect of the present invention, a sorting apparatus, such as sorting apparatus 20, is provided with sifting means positioned within receptacle 24 reversing the migration direction associated therewith for interacting with the microstructures to partially hinder the migration of the microstructures in the migration direction.

As is suggested in the exploded view of FIG. 2, one form of such a sifting means utilizable in accordance with the present invention is an array 38 of minute obstacles 39 upstanding from floor 28 of receptacle 24. Obstacles 39 are sized and separated as to advance the particular sorting objective of sorting apparatus 20. The manner of forming obstacles 39 of array 38, as well as a number of examples of embodiments of obstacles utilizable in such an array, will be discussed in substantial detail below.

Coverslip 36 is so secured to the top of obstacles 39 in array 38 as to preclude migration of microstructures between the obstacles 39 and coverslip 36. Coverslip 36 may optionally be transparent. In this form, coverslip 36 performs not only the function of the ceiling means described above, but also performs the function of a capping means for covering a shallow receptacle, such as receptacle 24, and for affording visual observation therethrough of the migration of microstructures through array 38. Coverslip 36 may be comprised of any ceramic material. Pyrex is preferred, but other materials such as quartz and sapphire, for example, may also be used.

In accordance with another aspect of the present invention, a sorting apparatus, such as sorting apparatus 20, is provided with electric force means for generating an electric field in the fluid medium in receptacle 24. The electric field induces the microstructures to migrate through the fluid medium, either from first end 32 to second end 34 or from second end 34 to first end 32, depending upon the polarity of the electric field and whether the microstructures are positively or negatively charged. Negatively charged microstructures, such as DNA molecules, will be induced to flow toward the positive pole. Positively charged microstructures, such as proteins, will be induced to flow toward the negative pole.

By way of example and not limitation, a first electrode 40 is shown in FIG. 2 as being located in first end 32 of receptacle 24 and a second electrode 42 located in second end 34 of receptacle 24. First electrode 40 and second electrode 42 each comprise a metal strip disposed on floor 28 of receptacle 24. In the preferred embodiment, the metal strip is formed from evaporated gold.

A battery 44, or other power source is electrically coupled between first and second electrodes, 40 and 42, such that first electrode 40 comprises a negative pole and second electrode 42 comprises a positive pole. The electric field generated between first and second electrodes, 40 and 42, is non-alternating, but the use of an alternating power source in place of battery 44 would be consistent with the teachings of the present invention.

When DNA is the microstructure being induced to migrate, the electric field intensity in receptacle 24 is in the range of from about 0.1 volt per centimeter to about 10 volts per centimeter. In the preferred embodiment, an electric field intensity is about 1.0 volt per centimeter.

Figure 3:
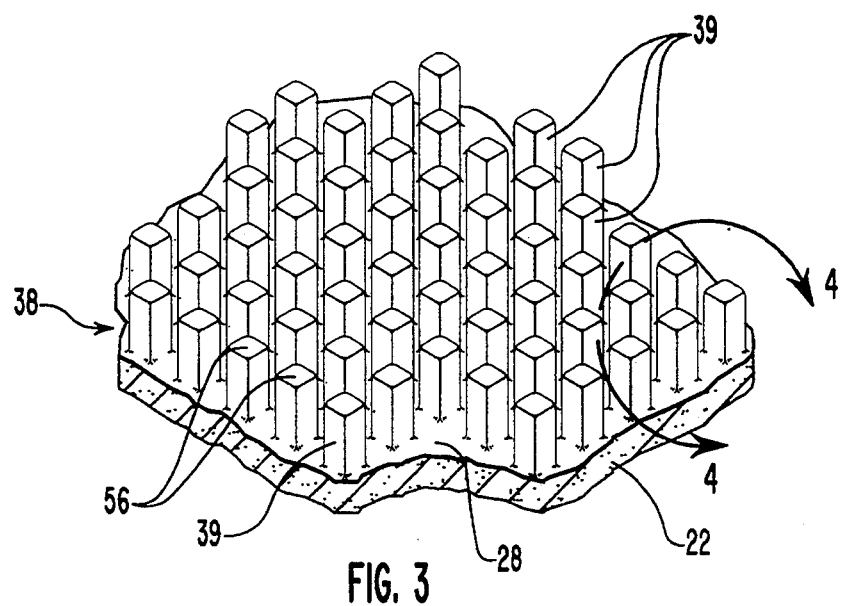
FIG. 3 is an enlarged view of the obstacles within the area of the array of FIG. 2 encircled by line 3—3 therein.

Referring now to FIG. 3, the portion of FIG. 2 encircled by line 3—3 is seen illustrated in an enlarged manner. FIG. 3 illustrates one example of a sifting means for use in a sorting apparatus of the present invention. As shown, array 38 comprises a plurality of obstacles 39 upstanding from floor 28 of receptacle 24. Although FIG. 3 illustrates obstacles 39 as being positioned within array 38 in an ordered and uniform pattern, it is within the scope of the present invention to have a staggered pattern, or any desired predetermined and reproducible pattern.

Figure 4:
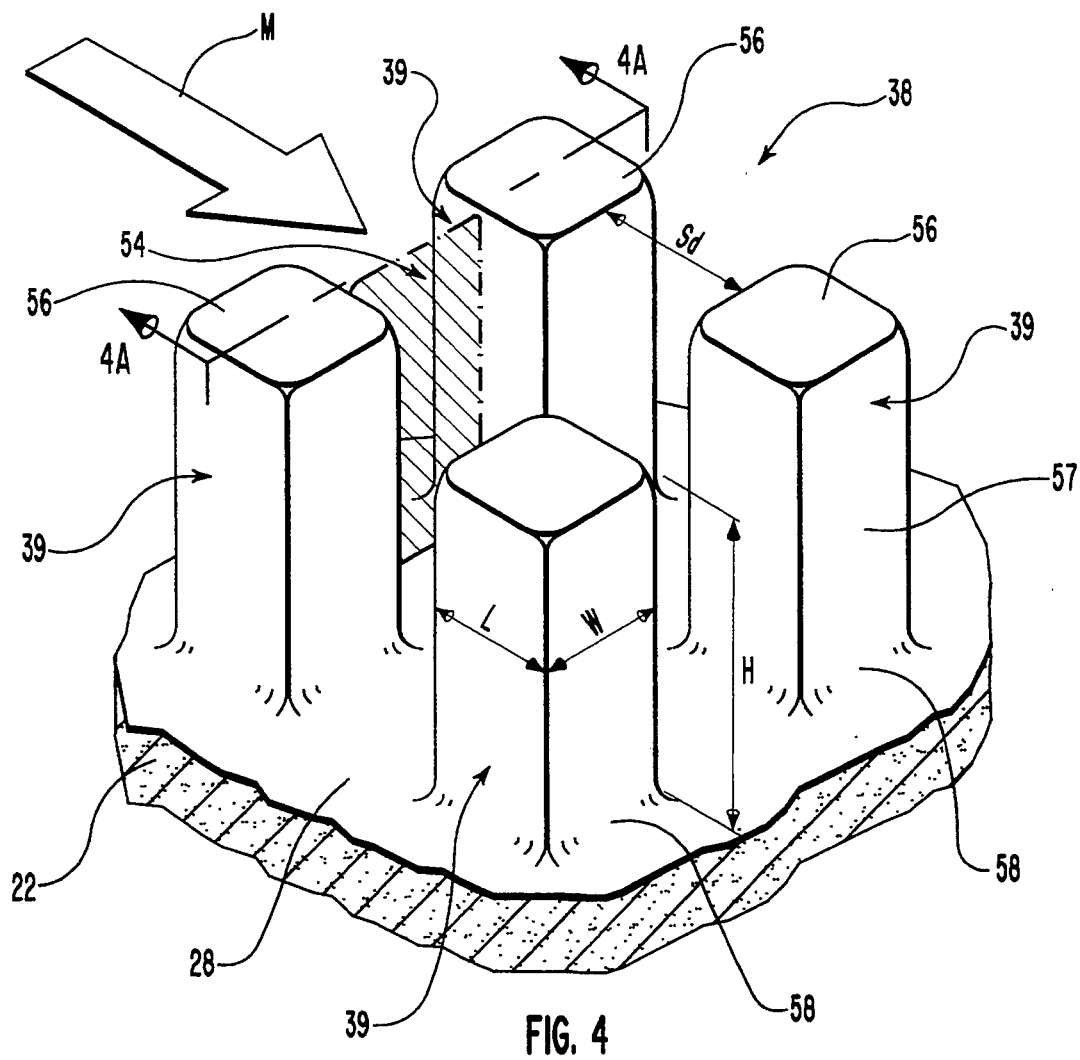
FIG. 4 is a further enlarged view of the obstacles within the area of the array of FIG. 3 encircled by line 4—4 therein.

FIG. 4 illustrates the various dimensions of a typical obstacle 39. The height H of obstacle 39 is measured in a direction normal to floor 28 of receptacle 24. The length L of obstacle 39 is measured in a direction parallel to said migration direction M. The width W of obstacle 39 is measured in a direction normal to the migration direction M. Each of the obstacles 39 are separated from an adjacent obstacle 39 by a predetermined separation distance $S_d$. The space between adjacent of obstacles 39 in a cross section of array 38 taken normal to floor 28 of receptacle 24 defines a pore 54 of the lattice structure cumulatively produced by obstacles 39 of array 38. For convenience of reference in FIG. 4, such a typical pore 54 has been shaded, but will be discussed in additional detail subsequently. These dimensions can be changed and designed to be as desired depending upon the type and size of microstructure to be sorted, the design of the array, and the type of obstacles in the array.

For example, the separation distance $S_d$ will vary depending upon whether the migration of microstructures through pores 54 are DNA molecules, viruses and bacterial cells, or mammalian cells. For migration of DNA molecules, the separation distance $S_d$ is within the range of about 0.01 microns to about 20.0 microns. For migration of viruses and bacterial cells, the separation distance $S_d$ is within the range of about 0.01 microns to about 1.0 micron. For migration of mammalian cells, the separation distance is within the range of from about 1.0 micron to about 50.0 microns. It is presently preferred that the separation distance $S_d$ be substantially equal to the radius of gyration of the molecule, the radius of gyration being the distance walking out from the center of the molecule.

Length L also varies depending upon the microstructure to be migrated through array 38 of obstacles 39. In a presently preferred embodiment, the length is generally equal to the separation distance. With regard to height H, the height of obstacles may generally be in the range of from 0.01 microns to about 20.0 microns. For smaller microstructures, the obstacles may have a height in a range from about 0.01 microns to about 0.50 microns. For larger microns, the height may be in the range from about 1.0 micron to about 5.0 microns.

Figure 4A:
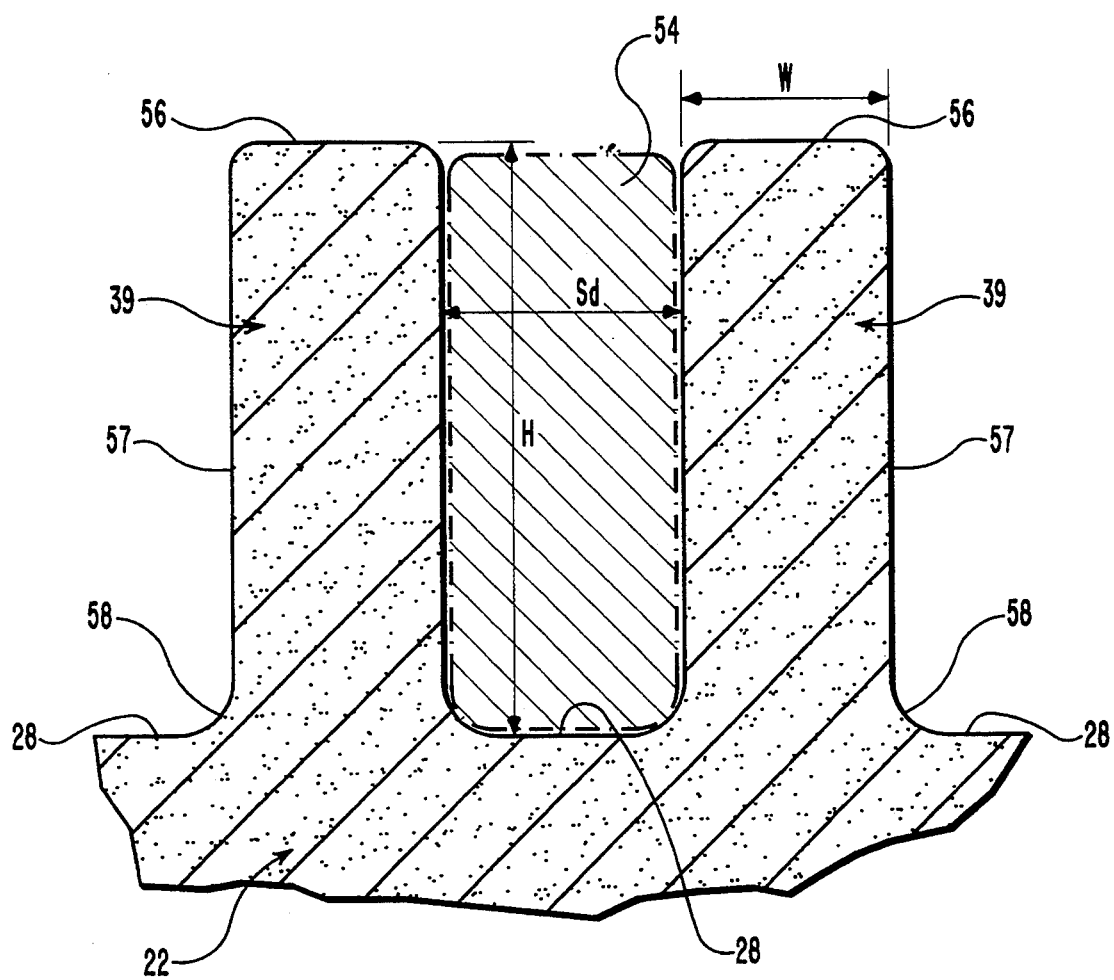
FIG. 4A is an elevational cross section view of two of the obstacles illustrated in FIG. 4 and the lattice pore therebetween taken along section line 4A—4A shown in FIG. 4.

FIG. 4A, a cross-section of two obstacles 39, illustrates in planar view a typical pore 54. Pore 54 compresses the area defined by two obstacles 39 through which a microstructure must pass. Pore 54 is defined by the height H and the separation distance $S_d$ between the obstacles. The desired size of pore 54 is determined by reference to the size of the microstructures to be sorted therethrough. An important aspect with the apparatus of the present invention is that not only is the pore size of the arrays known, but it is also constant and reproducible. More stable data can be obtained.

The characteristic number which sets the length scale for the conformation of a polymer in solution is the persistence length given by the equation:

$$P = \frac{EI_A}{K_B T}, \text{ where}$$

E is the Young's modulus,
$I_A$ is the surface moment of inertia,
$K_B$ is Boltmann's constant, and
T is the absolute temperature.

For DNA at normal physiological salt concentrations and pH, about 0.1M NaCl and pH 7.6, P is 0.06 microns.

If the etch depth of the array is approximately equal to or less than P then the polymer can be viewed as moving in a quasi-two-dimensional environment, as is the case in the apparatus used within the scope of the present invention.

In one preferred embodiment of a sorting apparatus, such as sorting apparatus 20, incorporating the teachings of the present invention, substrate 22 is provided with a receptacle 24 having sides 30 and 31 of approximately 3.0 millimeters in length and first and second ends 32, 34, respectively, of approximately 3.0 millimeters in length. Each of obstacles 39 has a height H of approximately 0.1 microns, a width W of approximately 1.0 micron, a length L of approximately 1.0 micron and a separation distance $S_d$ of approximately 2.0 microns. These sizes will vary depending upon the microstructure to be sorted, bearing in mind that obstacles 39 should be so sized and separated in array 38 that microstructures migrate through array 38 of obstacles 39 in essentially a single layer.

The method of making the apparatus of the present invention involves forming receptacle 24 on one side of substrate 22. Receptacle 24 should be formed of a size such that microstructures migrate in the fluid through receptacle 24 in essentially a single layer. A further step comprises creating array 38 of obstacles 39 within receptacle 24. Each of obstacles 39 have a top 56, sides 57, and a bottom end 58. Obstacles 39 are upstanding from floor 28 of receptacle 24 in a predetermined and reproducible pattern. In one preferred embodiment, the array of obstacles comprises a plurality of posts.

Figure 5A:
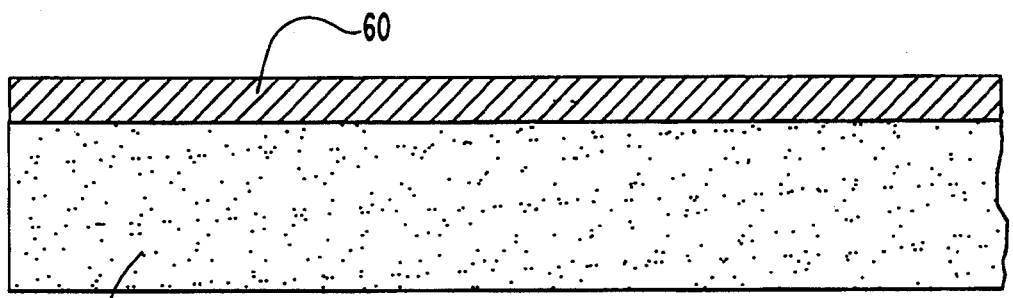
FIGS. 5A–5F illustrate the steps in a method for manufacturing a sorting apparatus, such as the sorting apparatus illustrated in FIG. 1.

By way of example and not limitation, the creation of posts within the receptacle is illustrated in FIGS. 5A-5F. As shown in FIG. 5A, the forming step comprises developing a photosensitive photoresist layer 60 over areas of substrate 22 that are intended to correspond to tops 56 of obstacles 39. This is accomplished by exposing substrate 22 to light through a mask having thereon a corresponding opaque pattern.

Figure 5B:
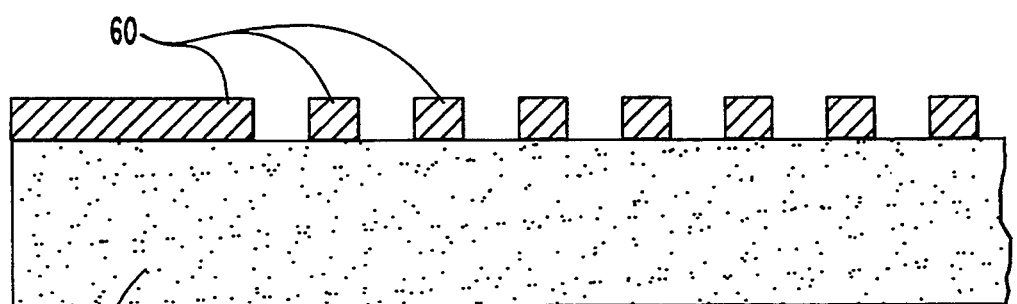

The portion of photoresist layer 60 which is exposed to light becomes soluble in a basic developing solution, while the unexposed portion remains on substrate 22 to protect substrate 22. Thus, after development in the developing solution, substrate 22 is left with a pattern of photoresist layer 60 that is identical to the opaque pattern of the mask. FIG. 5B illustrates substrate 22 with photoresist layer 60 thereon after exposure to light and development in solution.

Figure 5C:
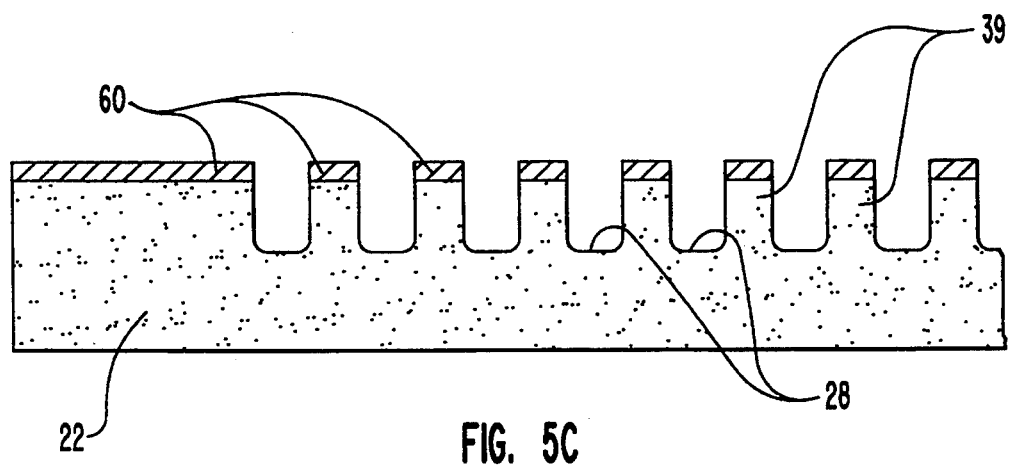

The next step comprises etching substrate 22 such that the areas of substrate 22 unshielded by photoresist layer 60 are exposed to the etching, thereby forming receptacle 24. The array 38 of obstacles 39 upstanding within the etched receptacle 24 is formed by the portions of substrate 22 shielded by photoresist layer 60. FIG. 5C illustrates formation of receptacle 24 and the obstacles 39.

As can be seen in FIG. 5C, as the substrate 22 is etched, the photoresist layer 60 is also etched, but at a slower rate. FIG. 5C illustrates the receptacle 24 half formed, and photoresist layer 60 partially etched away. If, for example, the photoresist layer is etched at a rate 1/10 the rate that substrate 22 is etched, the resulting receptacle can at most have a depth 10 times the thickness of the photoresist layer. The thickness of photoresist layer 60 must therefore be chosen accordingly.

Figure 5D:
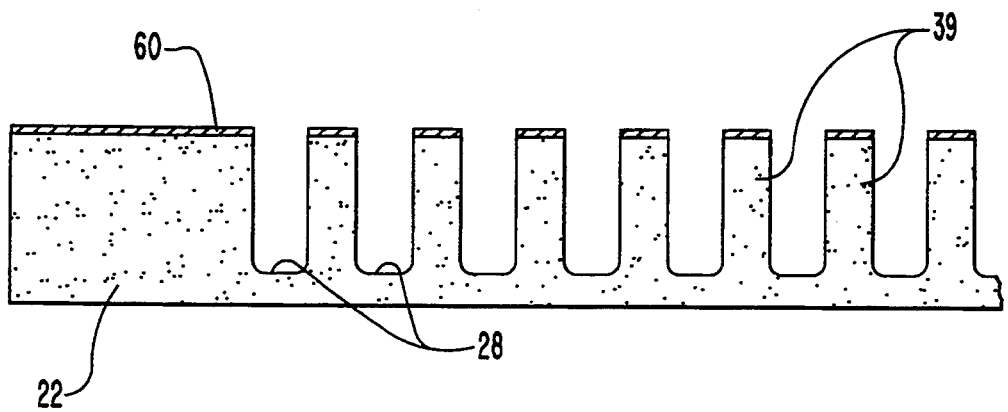
Figure 5E:
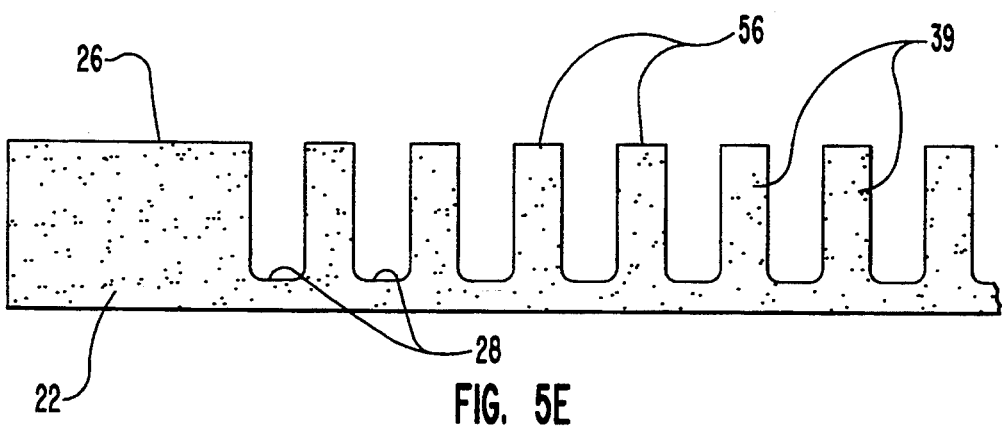

The etching process can be terminated at any time when the desired depth of the receptacle is reached. As illustrated in FIG. 5D, there may be some photoresist layer 60 still present on substrate 22 when the etching is terminated. If so, the next step is then dissolving photoresist layer 60 from substrate 22. This step leaves a clean substrate 22 as shown in FIG. 5E.

Within the scope of the present invention, etching may occur by many types of methods. In the preferred embodiment, ion milling is used such that an overhead ion beam is used to etch the substrate 22 and photoresist layer 60. Other methods of etching, such as chemical etching, are also within the scope of the present invention.

Figure 5F:
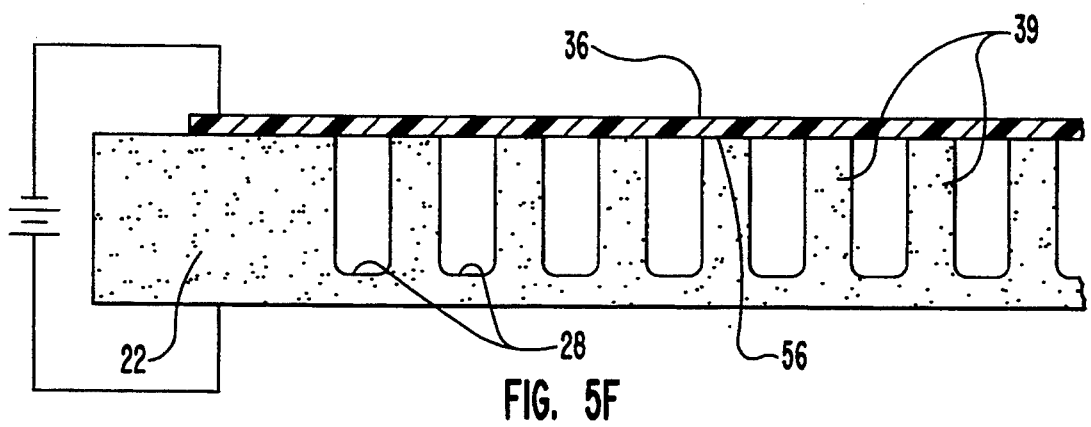

Turning now to FIG. 5F, the step of fusing coverslip 36 to substrate 22 is illustrated. In the preferred embodiment within the scope of the present invention, the step comprises positioning coverslip 36 over array 38 of obstacles 39 such that coverslip 36 is in contact with each of obstacles 39, and then applying an electric field between coverslip 36 and each of obstacles 39. The coverslip 36 is held with a negative potential. The obstacles 39 are held at a positive potential. Ions are thereby induced to migrate there between to create a bond between coverslip 36 and each of obstacles 39 at all areas of contact. The process of this step is referred to as field assisted fusion.

The voltage used to fuse coverslip 36 to the substrate 22 is preferably about 1 kilovolt but can be within the range of from 200 volts to about 2000 volts. The time for fusion is about 30 minutes at a temperature of about 400° C. The temperature can also range from about 300° C. to about 600° C., with 400° C. being the preferred temperature. In the preferred embodiment within the scope of the present invention, the coverslip comprises a pyrex material. However, any transparent ceramic may be used. For example, sapphire and quartz are material which may also be used for the coverslip.

It is preferred that the material used for coverslip 36 have substantially the same coefficient of thermal expansion as substrate 22. Otherwise, at the high temperature of fusion, the coverslip 36 and the substrate 22 will expand at different rates and a seal between the two would be difficult or impossible to accomplish.

Successful fusion can be tested by injecting a fluorescent fluid into the apparatus. A completely fused coverslip will not allow passage of any fluorescent fluid between coverslip 36 and obstacles 39.

Figure 6:
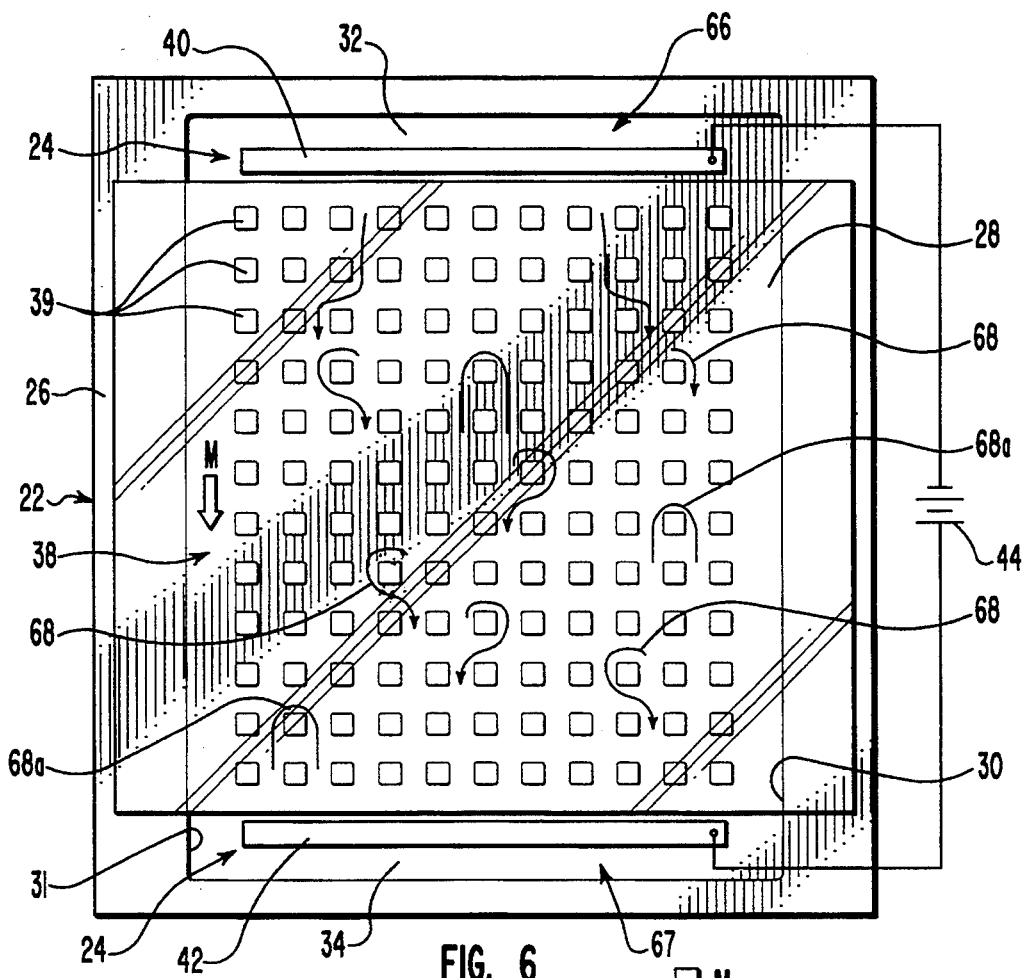
FIG. 6 is a plan view of the sorting apparatus shown in FIG. 1 with the obstacles enlarged to illustrate DNA molecules migrating through the array.

FIG. 6 illustrates one use of an embodiment of the present invention. As earlier stated, the apparatus of the present invention can be used for charged macromolecular electrophoresis. For example, the apparatus may be used to conduct protein electrophoresis, and DNA electrophoresis, with the positive and negative poles adjusted accordingly. FIG. 6 illustrates DNA electrophoresis.

As illustrated in FIG. 6 by way of example and not limitation, DNA molecules 68 are placed into a buffer solution and placed into a loading area 66 positioned on the first end 32 of receptacle 24. Loading area 66 comprises a portion of receptacle 24 where no obstacles 39 have been formed. Buffer is also added to a second loading area 67 positioned on second end 34. Second loading area 67 also comprises a portion of receptacle 24 where no obstacles have been formed. The loading areas are then covered.

Once DNA molecules 68 have been positioned, battery 44 is engaged and an electric field is generated. The electric field is so polarized as to induce the negatively charged DNA microstructures to migrate through the field from first electrode 40 toward second electrode 42 in receptacle 24.

As DNA molecules 68 migrate from first end 32 toward the second end 34, their movements are hindered by the array 38 of obstacles 39 upstanding within receptacle 24. Interaction between obstacles 39 and DNA molecules 68 are illustrated in FIG. 6.

In FIG. 6, DNA molecules 68 are illustrated as long arrows. The direction of the arrows indicates the direction of migration of DNA molecules 68. As DNA molecules migrate through array 38 of obstacles 39, large bodies of DNA molecules may become hooked by obstacles 39 and may become trapped. The hooked and trapped DNA molecules are labelled as 68a. When, as illustrated in FIG. 6, obstacles 39 are posts, DNA molecules 68 stretch around obstacles 39 as they become hooked. The obstacles are thought to catch the large DNA molecules and hold them against the electric field. Some DNA molecules 68 may stretch and release themselves from the obstacles. Smaller DNA molecules possess sufficient Brownian motion to release themselves.

It is an important feature of the present invention that any pattern of array 38 of obstacles 39 can be designed within the scope of the present invention. The array 38 can comprise an ordered, evenly spaced formation wherein the obstacles are positioned in uniform rows and columns. Alternatively, array 38 may comprise a staggered formation wherein positioning of the obstacles is not uniform but rather scattered around the array. Further, array 38 may comprise a mixture of such arrangements disposed along migration direction M traversing same.

The design of the array can be formulated to correspond to any specific intended use. The ordered, evenly spaced configuration can be used for imaging of long megabase DNA fragments. The staggered configuration, having a higher possibility of hooking the DNA molecules as the DNA molecules migrate through the array, can be used to more directly test the role of DNA relaxation and hooking in the mobility of DNA molecules.

Figure 7:
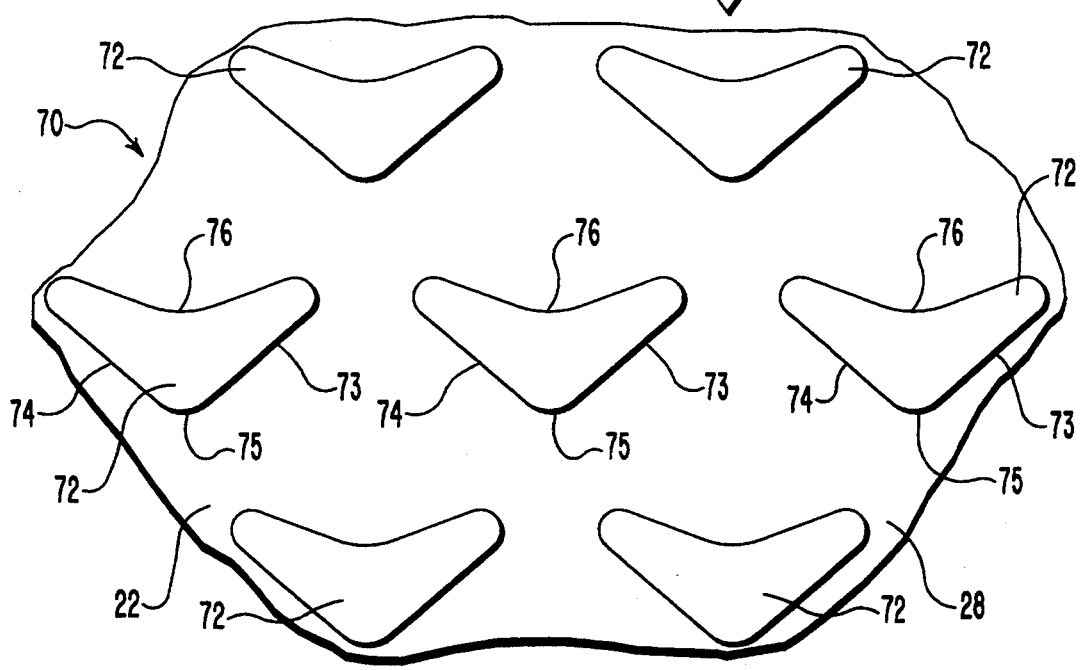
FIG. 7 is a plan view of an alternate embodiment of obstacles usable in an array in a sorting apparatus incorporating the teachings of the present invention wherein the obstacles are v-shaped.

The shapes of the obstacles may also vary within the scope of the present invention. Illustrated in FIG. 7 is an array 70 of v-shaped obstacles 72 upstanding from floor 28 of receptacle 24, and having a v-shaped cross section in a plane disposed parallel to floor 28 of receptacle 24. Arms 73 and 74 intersect at one end to form a vertex 75 and an open end 76. The open end 76 of said v-shaped cross section of v-shaped obstacles 72 is disposed opposing migration direction M of receptacle 24.

The size of v-shaped obstacles 72 should be such that as microstructures of various sizes migrate through the array 70 of v-shaped obstacles 72 in a direction M, the microstructures are hindered and trapped within the open end 76 of v-shaped obstacles 72. Smaller v-shaped obstacles 72 will trap small microstructures while larger v-shaped obstacles 72 will trap both the smaller and the larger microstructures.

It is conceivable that various sizes of v-shaped obstacles 72 may be used within one array 70. For example, smaller v-shaped obstacles 72 may be positioned toward the first end 32 of receptacle 24 with larger v-shaped obstacles 72 positioned toward the second end 34 of receptacle 24. Thus, as the microstructures migrate from first end 32 toward second end 34, the smaller microstructures will become trapped in the smaller v-shaped obstacles 72 while the larger microstructures will flow past the smaller v-shaped obstacles 72. As the larger microstructures flow through the larger sized v-shaped obstacles 72, the larger microstructures will also become trapped. The microstructures will then be separated with respect to size.

Figure 8:
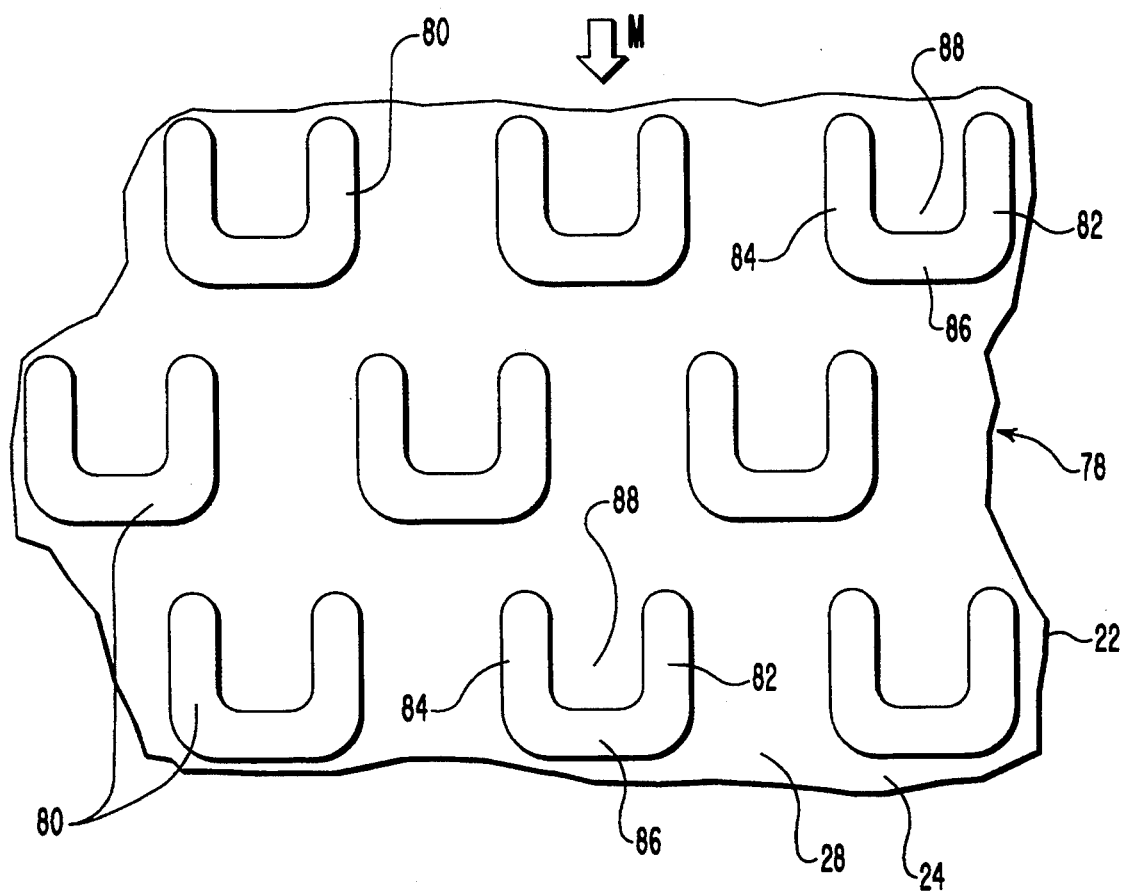
FIG. 8 is a plan view of another alternate embodiment of obstacles usable in an array in a sorting apparatus incorporating the teachings of the present invention wherein the obstacles are cup-shaped.

Referring now to FIG. 8, an alternate embodiment of the array of obstacles within the scope of the present invention is illustrated. FIG. 8 illustrates an array 78 of obstacles 80 which are cup-shaped. Obstacles 80 have a cup-shaped cross section in a plane disposed parallel to floor 28 of receptacle 24.

As illustrated, cup-shaped obstacles 80 may comprise a first leg 82 and a second leg 84 substantially parallel to the direction of migration of the microstructures, and a third leg 86 substantially perpendicular to the direction of migration. First, second, and third legs, 82, 84, and 86, respectively, are positioned such that they define an open end 88 into which the microstructures can become trapped as the microstructures migrate through the cup-shaped obstacles 80. As with v-shaped obstacles 72, various sizes of cup-shaped obstacles 80 may be positioned within array 78 in any pattern desired. The open end 88 of the cup-shaped cross-section is disposed opposing migration direction M of receptacle 24.

It is important to note that whatever type of array is used, the array is reproducible. Additionally, an optimum design can be perfected over time by making minor changes to the arrays for each new experiment until the most preferred design is obtained.

Figure 9:
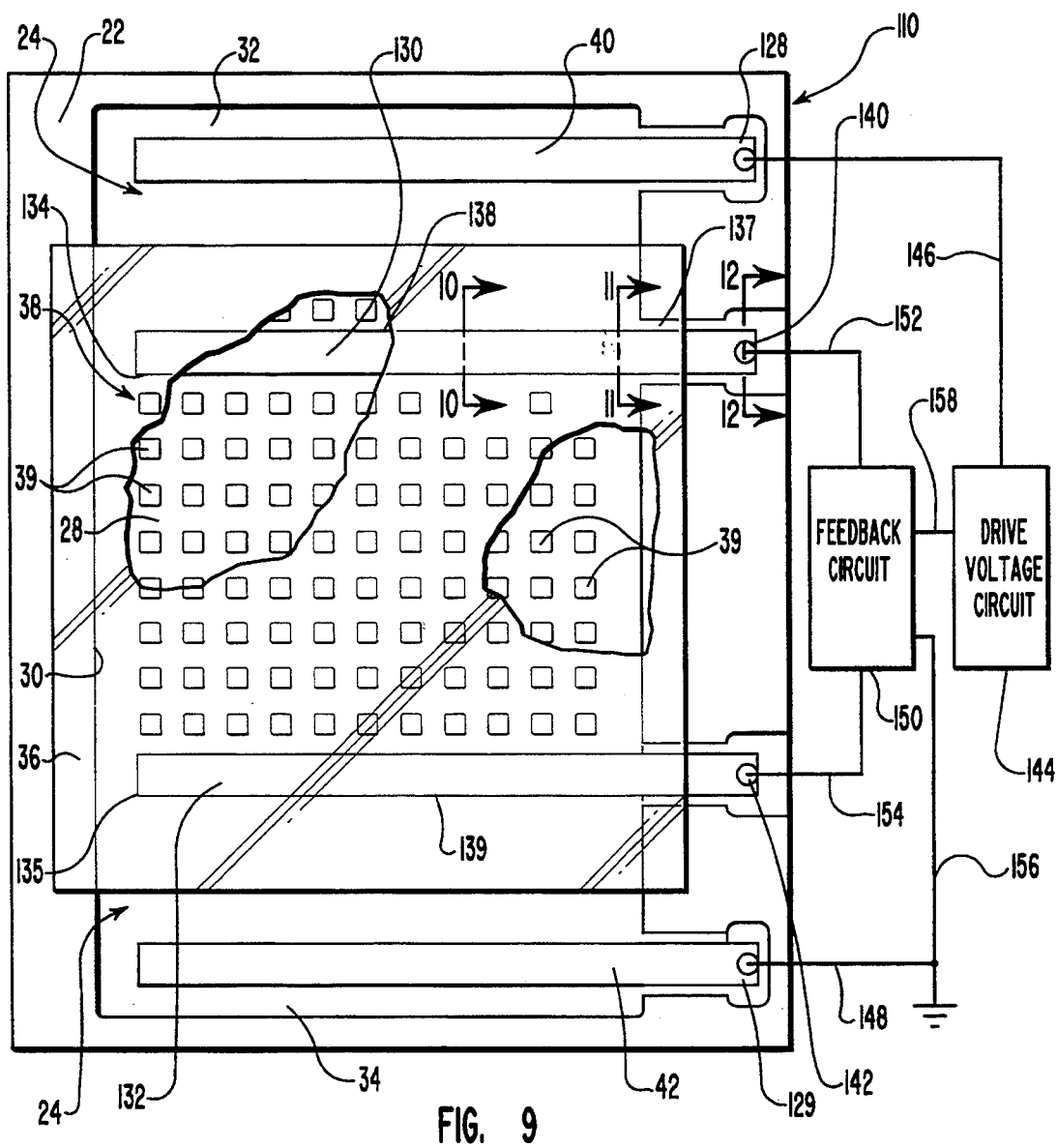
FIG. 9 is a plan view of yet another embodiment of a sorting apparatus incorporating the teachings of the present invention in which a pair of sensor electrodes are located within the array of the sorting apparatus.

Referring now to FIG. 9, and in accordance with another aspect of the present invention, a sorting apparatus 110 is comprised of an apparatus, such as sorting apparatus 20, further provided with sensor means for detecting the intensity of the electric field generated within the array of obstacles, such as array 38 of obstacles 39, between any determined first and second points therein, to enable control of the intensity of the electric field.

Sorting apparatus 110 is illustrated in FIG. 9. As in sorting apparatus 20, shown in FIGS. 1 and 2, sorting apparatus 110 includes first electrode 40 and second electrode 42, functioning as negative and positive poles, for an electric field generated therebetween. That field may be non-alternating, by coupling therebetween a battery, such as battery 44 of FIGS. 1 and 2. Nevertheless, it would also be consistent with the teachings of the present invention to develop an electric field that is alternating or switchable as to polarity, either selectively or according to some repeated pattern. In the case of sorting apparatus 110, however, the electric field developed between first and second electrodes 40 and 42 is produced by a feedback varied drive voltage circuit 144 that will be explored in detail subsequently.

First electrode 40 comprises a metal strip positioned along floor 28 of receptacle 24 at first end 32. First electrode 40 is soldered to substrate 22 and to various lead lines at a first area 128. Second electrode 42 comprises a metal strip positioned along floor 28 of receptacle 24 at second end 34. Second electrode 42 is soldered to substrate 22 and to various lead lines at a second area 129. In the preferred embodiment, the metal strips, first and second electrodes 40 and 42, comprise gold evaporated into floor 28.

Positioned within the array is sensor means for detecting the intensity of the electric field generated between first electrode 40 and second electrode 42 between predetermined first and second points therein. The sensor means enables control of the intensity of the electric field generated.

The sensor means comprises a first sensor electrode 130 positioned within array 38 of obstacles 39 at the first predetermined point 134. The sensor means further comprises a second sensor electrode 132 which is positioned within array 38 of obstacles 39 at the second predetermined point 135. First sensor electrode 130 is positioned within array 38 toward first end 32 of receptacle 24 in a first sensor channel 138 formed along floor 28 of receptacle 24. No obstacles 39 are present within channel 138. A clear area is formed wherein the sensor electrode is positioned.

In one embodiment of the present invention, the array 38 is turned at a 45 degree angle before the sensor electrodes are positioned within the array.

As can be seen in FIG. 9, first and second sensor electrodes, 130 and 132, extend through sidewall 31 of receptacle 24, past coverslip 36, and onto substrate 22. Positioning of first sensor electrode 130 can be seen in FIGS. 10–12.

Figure 10:
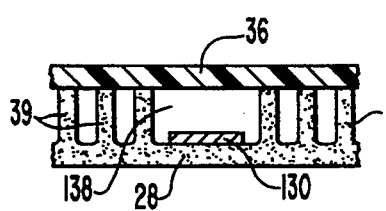
FIG. 10 is a cross sectional elevation view of the apparatus shown in FIG. 9 taken along section line 10—10 shown therein, illustrating positioning of the top sensor electrode within the array of obstacles.

In FIG. 10, first sensor electrode 130 is shown disposed along floor 28 of receptacle 24 within first sensor channel 138. Obstacles 39 can be seen positioned along the sides of top sensor channel 138, but not within channel 138 itself. Coverslip 36 is shown fused to the obstacles 39 and covering channel 138.

Figure 11:
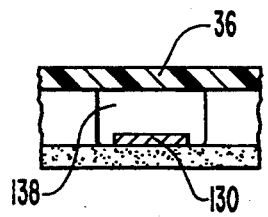
FIG. 11 is a cross sectional elevation view of the apparatus shown in FIG. 9 taken along section line 11—11 shown therein, illustrating positioning of the top sensor electrode.

FIG. 11 illustrates channel 137 extending away from sidewall 31 of receptacle 24. Obstacles are not present within channel 137. Coverslip 36 is illustrated in FIG. 11 as positioned over channel 137.

Figure 12:
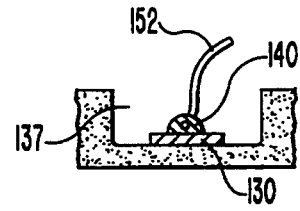
FIG. 12 is a cross sectional elevation view of the sensing apparatus shown in FIG. 9 taken along section line 12—12 shown therein, illustrating positioning of the top sensor electrode outside of the array of obstacles.

FIG. 12 illustrates the first sensor soldering area 140 where first sensor electrode 130 is soldered to the substrate 22 and connected to first sensor lead 152, to be later discussed in more detail.

Although cross sections for only first sensor electrode 130 are shown, it must be noted that second sensor electrode 132 is positioned within apparatus 110 in the same fashion. Second sensor electrode 132 is positioned within a bottom sensor channel 139 within the array 38 of obstacles 39. Second sensor electrode 132 is soldered to substrate 22 and connected to a second sensor lead 154 at a second sensor soldering area 142. Second sensor lead 154 will be later discussed in more detail.

First electrode 40 is electrically coupled to drive voltage circuit 144 by first electrode lead 146 soldered to first electrode 40 at a first electrode soldering area 128. Second electrode 42 is grounded by way of a first ground lead 148 that is connected to second electrode 42 at a second electrode soldering area 129.

First and second sensor electrodes, 130 and 132, are electrically coupled to each other and to drive voltage circuit 144 through a feedback circuit 150. A first sensor electrode lead 152 connects the first sensor electrode 130 to feedback circuit 150. A second sensor electrode lead 154 connects the second sensor electrode 132 to feedback circuit 150.

A second ground lead 156 connects feedback circuit 150 to the ground. A control lead 158 connects feedback circuit 150 to drive voltage circuit 144.

Figure 13:
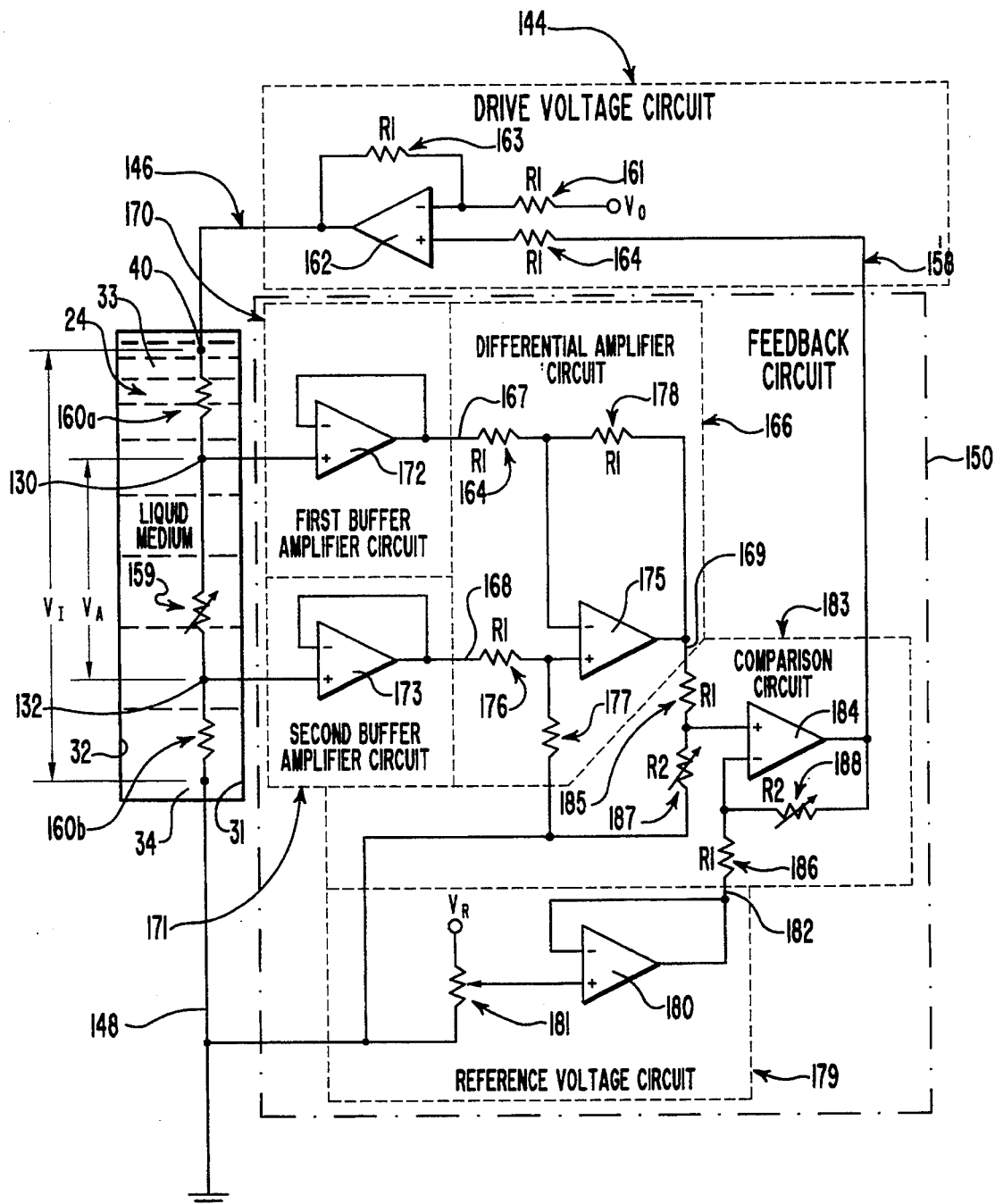
FIG. 13 is an electrical schematic diagram of the feedback circuit associated with the pair of sensor electrodes shown in the embodiment of the sensing apparatus illustrated in FIG. 9.

As shown by way of example, the specific structural details of one embodiment of a feedback circuit, such as feedback circuit 150 in FIG. 9, and a drive voltage circuit, such as drive voltage circuit 144 in FIG. 9, can be appreciated by reference to FIG. 13.

As shown in FIG. 13 for purposes of illustration, receptacle 24 is filled with a liquid medium in which the input voltage $V_I$ supplied between first electrode 40 and grounded second electrode 42 creates an electric field.

The actual voltage $V_A$ created in the liquid medium in receptacle 24 between first sensor electrode 130 and second sensor electrode 132 is illustrated as a voltage drop occurring over a variable resistor 159. Resistor 159 represents the resistance to the electric field presented in the liquid medium in receptacle 24 between the first and second predetermined points in array 38. In operation of a sorting apparatus such as sorting apparatus 110, the composition of the liquid medium will vary from a number of causes. This as a result varies the electrical resistance of the liquid medium.

The actual voltage $V_A$ inherently differs from the input voltage $V_I$ by the amount of voltage drop occurring in the liquid medium at two locations. These are between first electrode 40 and first sensor electrode 130 and between second sensor electrode 132 and second electrode 42. The resistance in the liquid medium in receptacle 24 between first electrode 40 and first sensor electrode 130 is illustrated as a resistor 160$a$, while the corresponding resistance between second sensor electrode 132 and second electrode 42 is illustrated as a resistor 160$b$.

FIG. 13 illustrates in addition an exemplary arrangement of circuit elements intended to perform the functions of drive voltage circuit 144 and feedback circuit 150 illustrated in FIG. 9.

In an aspect of the present invention discussed relative to sorting apparatus 20, a sorting apparatus, such as sorting apparatus 110, is also provided with electric force means for generating the electric field in the fluid medium in receptacle 24. In sorting apparatus 20 illustrated in FIG. 1, one example of such an electric force means was illustrated in the form of battery 44.

In FIG. 9, however, an alternative form of such an electric force means is illustrated in the form of drive voltage circuit 144. Shown in more detail in FIG. 13, drive voltage circuit 144 comprises an original voltage $V_0$ which is coupled through an input resister 161 to the negative terminal of a differential amplifier 162. In this manner, the voltage appearing on first electrode lead 146 coupled to the output terminal of differential amplifier 162 has an inverse polarity relative to input voltage $V_0$. A biasing resister 163 is coupled in parallel between the negative input terminal of differential amplifier 162 and the output terminal thereof.

While in some embodiments, input voltage $V_0$ may comprise a battery, it is also the intention in sorting apparatus 110 to afford for an input voltage $V_0$, which can itself be variable and which, due to the coupling thereof through the negative input terminal of differential amplifier 162, is inversely variable relative to the input voltage $V_I$ that is eventually supplied over first electrode lead 146 to first electrode 40.

According to one aspect of the present invention, a sorting apparatus, such as sorting apparatus 110 illustrated in FIG. 9, includes sensor means for detecting the intensity of the electric field generated within the liquid medium in receptacle 24 in any preselected portion of array 38. The electric field detected corresponds to actual voltage $V_A$ illustrated in FIG. 13. In FIG. 13 the preselected portion of array 38 over which actual voltage $V_A$ is measured is located between a first predetermined point 134 in array 38 corresponding to first sensor electrode 130 and a second predetermined point 135 therein corresponding to second sensor electrode 132.

FIG. 13 illustrates an example of circuit elements capable of performing the function of such a sensor means for use in a sorting apparatus incorporating teachings of the present invention. These elements include first sensor electrode 130 positioned within array 38 of obstacles 39 at first predetermined point 134 and a second sensor electrode 132 positioned within array 38 at second predetermined point 135. In combination therewith, the sensor apparatus according to the teachings of the present invention comprises control means coupled to first sensor electrode 130 and second sensor electrode 132 for maintaining the electric field in the liquid medium in receptacle 24 at a predetermined intensity.

The elements of one embodiment of such a control means are shown in FIG. 13 in the form of the circuit components and functional groupings thereof that comprise feedback circuit 150. Feedback circuit 150 functions to vary the voltage supplied by drive voltage circuit 144 to first electrode 40 utilizing a control signal supplied thereto over control lead 158. While the elements of feedback circuit 150 will be described in detail subsequently, the effect of the control signal supplied over control lead 158 to drive voltage circuit 144 will be better appreciated fully by an initial discussion of the constituent elements of drive voltage circuit 144.

The control signal from control lead 158 is applied to the positive input terminal of differential amplifier 162 through a second input resistor 164. The effect of the control signal on control lead 158 is to vary the output of drive voltage circuit 144 on first electrical lead 146 with the object of stabilizing actual voltage $V_A$. To do so the intensity of the electric field in the fluid medium in receptacle 24 is increased, when the control signal indicates that the actual voltage $V_A$ is less than some predetermined referenced voltage desired by the operator of sorting apparatus 110. Correspondingly, the control signal of control lead 158 is oppositely polarized and thus decreases the intensity of the electric field in the liquid medium in receptacle 24, when the control signal reflects that the actual voltage $V_A$ is greater than that same predetermined reference voltage. In this manner, the control signal supplied on control lead 158 to drive voltage circuit 144 will by the action of differential amplifier 162 adjust the actual effect of original voltage $V_0$ so as to maintain the actual voltage $V_A$ at any desired level.

The use of the control signal supplied over control lead 158 to drive voltage circuit 144 could be utilized as a mechanism for effecting desired variations in the voltage supplied to first electrode 40 on first electric lead 146. Under most circumstances, however, it is anticipated that the known propensity of a liquid medium in which microstructures are migrating will vary during the time of operation due to a number of factors, such as evaporation, chemical reactions, and temperature changes. An initial objective of the circuitry that will now be described relative to feedback circuit 150 is to compensate for what is in effect the changeable nature of the liquid medium in receptacle 24 as illustrated by variable resistor 159. In this manner actual voltage $V_A$ is maintained at some predetermined constant intensity.

As illustrated in FIG. 13, feedback circuit 150 includes a differential amplifier circuit 166 having a first input terminal 167, a second input terminal 168, and an output terminal 169. First input terminal 167 is coupled through a first buffer amplifier circuit 170 to first sensor electrode 130, while second input terminal 168 is coupled through a second buffer amplifier circuit 171 to second sensor electrode 132.

First buffer amplifier circuit 170 is comprised of a differential amplifier 172 connected in the manner illustrated between the circuit components already described above. Correspondingly, second buffer amplifier circuit 170 is comprised of a differential amplifier 173 connected as illustrated. It is the function of first and second amplifier circuits 170, 171, respectively, to serve as impedance buffers for first and second input terminals 167, 168, respectively, of differential amplifier circuit 166.

Within differential amplifier circuit 166, first input terminal 167 is coupled through an input resistor 174 to the negative input terminal of a differential amplifier 175, while second input terminal 168 is coupled to the positive terminal thereof through an input resistor 176. Resistors 177 and 178 are connected as shown in FIG. 13 to bias differential amplifier 175 into the desired operator thereof. By the arrangements illustrated and described, differential amplifier circuit 166 produces at output terminal 169 thereof an output signal that corresponds to the intensity of actual voltage $V_A$ of the electric field in the liquid medium in receptacle 24.

According to another aspect of the present invention, a feedback circuit, such as feedback circuit 150, includes a comparator means coupled to output terminal 169 of differential amplifier circuit 166 for producing a control signal at control lead 158 that reflects the difference between the output signal on output terminal 169 and a reference voltage reflecting a predetermined desired intensity of actual voltage $V_A$.

As shown by way of example and in FIG. 13, such a reference voltage is supplied by a reference voltage circuit 179 which comprises a differential amplifier 180 having a reference voltage $V_R$ coupled to the positive input terminal thereof through a variable resistor 181. In this manner, variable resistor 181 can be used to adjust the effect of reference voltage $V_R$ appearing at the output side of differential amplifier 180 at an output terminal 182 for reference voltage circuit 179.

It is the purpose of comparison circuit 183 illustrated in FIG. 13 to produce on control lead 158 a control signal reflecting the difference, if any, between the output signal appearing at output terminal 169 of differential amplifier circuit 166 and the portion of reference voltage $V_R$ appearing at output terminal 182 of reference voltage circuit 179. Toward that end, comparison circuit 183 comprises a differential amplifier 184 coupled at the output terminal thereof to control lead 158. The positive input terminal of differential amplifier 184 is coupled through an input resistor 185 to output terminal 169 of differential amplifier circuit 166, while the negative input terminal of differential amplifier 184 is coupled through an input resistor 186 to output terminal 182 of reference voltage circuit 179. Variable resistors 187, 188 are connected as shown within comparison circuit 183 to effect desired biasing of differential amplifier 184.

In the circuitry illustrated in FIG. 13, differential amplifiers 162, 172, 173, 175, 180, and 184 can, by way of example, comprise operational amplifiers available from Analog Devices as Product No. AD795N. Such devices utilize field effect transistor inputs and have low noise characteristics. The values of the resistors illustrated are as follows:

$R_1 = 10$ k$\Omega$
$R_2 = 10^6 \Omega$

For an apparatus, such as sorting apparatus 110, original voltage $V_O$ is equal to negative 15 volts, while reference voltage $V_R$ is equal to positive 15 volts.

Figure 14:
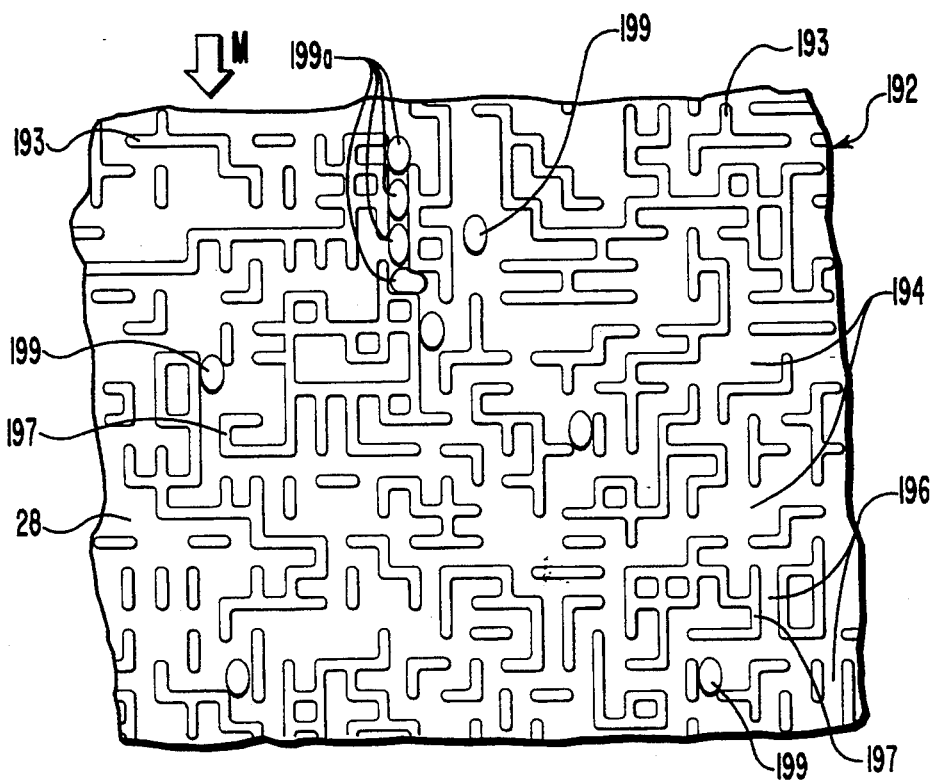
FIG. 14 is an enlarged plan view of another embodiment within the scope of the present invention illustrating a portion of a percolating array having cells migrating therein.

By means of the circuitry illustrated in FIG. 14, any desired predetermined actual voltage $V_A$ can be maintained between first and second sensor electrodes 130, 132, respectively, despite variations over time in the nature of the liquid medium in receptacle 24.

It must be noted that although an electric field has been described in detail as the means for inducing migration of the microstructures, other fields such as hydrodynamic, magnetic, and gravity, for example, may also be used.

B. Cell Fractionation

FIGS. 14–18 illustrate another use of the teachings of the present invention to facilitate the study of the motion of cells, such as human red blood cells, bacterial cells, and cancer cells, for example, through channels in a single layer and in single file. For red blood cells, the channels may simulate those found in capillaries, the lung alveoli, and the spleen in the human body. Further, with the apparatus of the present invention, red blood cells can be fractionated on the basis of physical properties which are otherwise difficult to probe by biological markers.

The apparatus within the scope of the present invention comprises channeling means positioned within receptacle 24 for allowing passage of cells through receptacle 24 in essentially a single layer and in single file.

One possible configuration of an array for all fractionation within the scope of the present invention is illustrated in FIG. 14. This array 192 is called a percolating array and is patterned as a maze. In this configuration, the channeling means comprises obstacles 193 positioned upstanding from floor 28 of receptacle 24 in various connecting positions to form open areas 194, passageways 196, and dead ends 197, such as are found in mazes. As can be seen in FIG. 14, cells 199 migrate through percolating array 192 through open areas 194 and passageways 196 and are at times blocked by dead ends 197. Passageways 196 may be made linear, curved, or whatever shape desired so as to be able to observe migration of cells through variously shaped passageways. Passageways 196 may have a width in the range of from about 1.0 micron to about 10.0 microns and a depth with the range of from about 1.0 micron to about 10.0 microns. Cells migrating in single file can be seen labelled as 199a.

Percolation, as herein discussed, is the phenomenon of increasing path connectedness due to random addition of discrete segments to allowed motion. At the percolation threshold, there is just one path on the average through the array, with all other paths leading to dead ends. The ability of cells to find that path can be observed with the percolating arrays 192 of the present invention.

Within the scope of the present invention, percolating arrays 192 have been constructed on a rectangular lattice in a preferred percolating embodiment. A single computer algorithm fills some fraction of the lattice with lines, for example, 40% so as to form the variety of open areas 194 and passageways 196. The computer program is then made into the opaque mask and the microlithographic process as earlier described is carried out.

In the preferred embodiment, the obstacles 193 are comprised of barriers 5.0 microns long and 1.0 micron wide. The preferred etch depth of percolating array 192 is 0.35 microns. FIG. 14 illustrates an enlarged section of such a photomicrograph percolating array 192.

One example of the use of percolating array 192 is for study of the movements of cells, such as *E. coli*, from one end of array 192 to the other. In one experiment, *E. coli* cells were placed at the first end 32 of receptacle 24 while food was placed at the second end 34 of receptacle 24. The *E. coli* cells were then observed as they migrated in a single layer through percolating array 192 from first end 32 toward second end 34. When dead ends 197 were reached by the *E. coli* cells, the manner in which the *E. coli* cells reoriented themselves in order to move away from the dead ends 197 was observed. Also observed was the ability of the *E. coli* cells to find an open path from the starting point at first end 32 to the food at second end 32.

The studies conducted for the *E. coli* cells can also be conducted for many other types of cells. Percolating arrays 192 can be used to study the manner in which many other types of free floating cells reorient themselves in a fluid suspension when confronted with barriers and passageways, and the manner in which various passageways are chosen.

As earlier stated, the percolating arrays 192 are formed such that migration of a cell in a single layer and single file can be observed. Therefore, in order to accommodate the various sizes of cells to be observed, the size of open areas 194 and passageways 196 in each array 192 can be designed as needed. The pattern of the array can also be designed as desired. Any pattern can be produced and reproduced.

One additional important aspect of percolating arrays 192 is the ability to perform electrophoresis of charged spherical balls within percolating arrays 92. The mobilities of even simple balls are rich in a percolating array because of the numerous dead-ends that exist in a percolating array near the percolating threshold. If the electric fields are too big, then the balls cannot back-diffuse out of the dead end against the applied electric force. Hence, mobility shuts down above a critical field. Measuring the diffusion of fluorescent balls of precise diameter will allow study of a diffusion of polymers in arrays.

Figure 15:
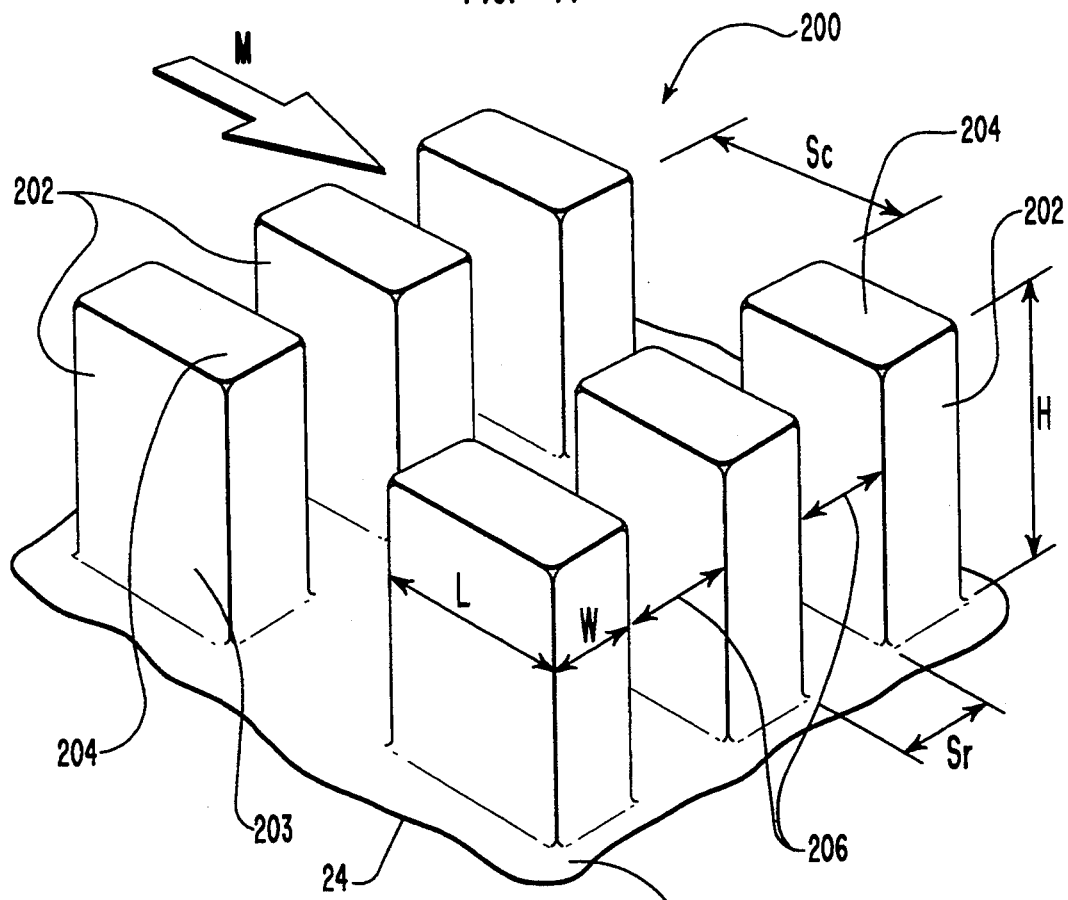
FIG. 15 is a perspective enlarged view of an alternate embodiment of obstacles for an array in a sorting apparatus incorporating the teachings of the present invention to stimulate cell behavior simulating the passage of such cells through the passageways in the human body.

Referring now to FIG. 15, another embodiment of the present invention can be seen. In FIG. 15, an array 200 of obstacles in the form of elongated rectangular bunkers 202 is positioned within receptacle 24. Bunkers 202 are comprised of a rectangular shape having opposing sidewalls 203 and a top 204. Bunkers 202 upstand from floor 28 of receptacle 24. Bunkers 202 are positioned within columns and rows within receptacle 24. Cells migrate through the columns and between the rows of bunkers 202 in a migration direction indicated by arrow M. The longitudinal axis of the bunkers are disposed in alignment with migration direction M. Channels 206 are formed between rows of bunkers 202 through which the cells migrate. A separation distance, $S_r$, between rows of bunkers 202, indicates the size of channels 206.

While the size and organization of bunkers 202 may vary, in a preferred embodiment within the scope of the present invention, the separation distance $S_r$ is sized to allow the cells to migrate through channels 206 in essentially a single layer in single file.

The height H of each bunker 202 should also be such that it allows the cells to pass through the bunkers 202 in essentially a single layer. As with the apparatus for fractionating DNA, a coverslip 36 is fused to the tops 204 of bunkers 202 so as to prevent migration of cells between the coverslip and the tops 204 of bunkers 202 to ensure that the cells migrate through the array 200 of bunkers 202 in essentially a single layer.

While bunkers 202 are the preferred obstacles for forming channels 206, different structures may also be used to simulate channels through which the cells can migrate and be observed. These alternate structures are also within the scope of the present invention.

Figure 16:
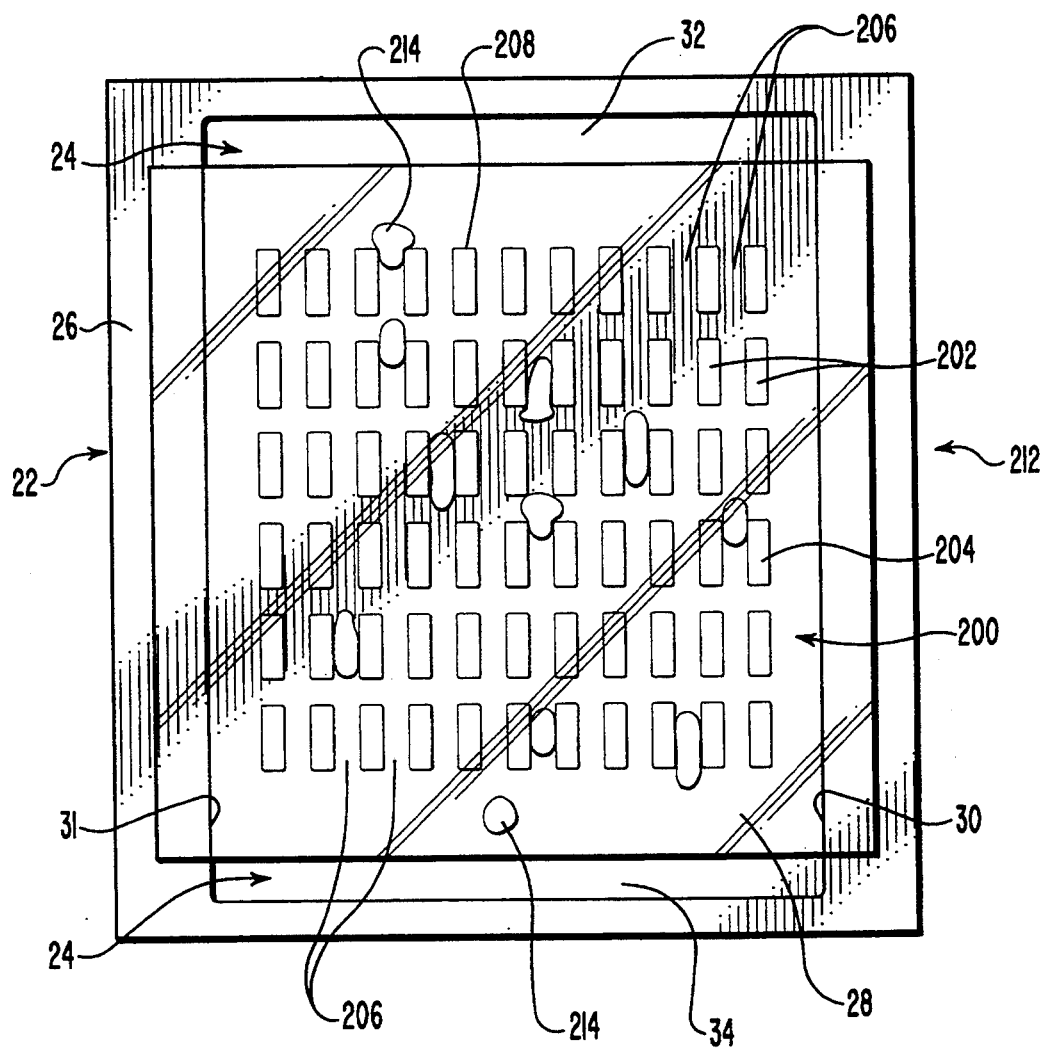
FIG. 16 is a plan view of an embodiment of a sorting apparatus incorporating the teachings of the present invention utilizing obstacles of the type shown in FIG. 15 enlarged to illustrate cells deforming to migrate through the array thereof.

FIG. 16 illustrates an apparatus 212 for cell sorting and fractionation. As an example, and not as a limitation, cells 214 are shown migrating through array 200 of bunkers 202. Cells 214 can be seen moving between the rows of bunkers 202 through channels 206. Some cells begin round, deform to fit within channels 206, and then regain their shape once out of the channel. Other cells which may have lost some degree of deformability, however, do not regain their shape, or are misshapen initially. Some are even trapped in these, restricted channels. This, as earlier stated, can be caused by aging, sickling or other in vivo or in vitro problems.

For illustration, cells 214 are shown to be disc shaped. As cells 214 enter channels 206, cells 214 deform from a disc shape to an elongated shape so as to be able to squeeze through channels 206. When cells 214 are positioned between bunkers 202 and within channels 206, cells 214 have a thin elongated shape. As cells 214 move from between bunkers 202 and into open space, the healthy cells 214 can be seen to resume their original disc shapes. The unhealthy cells may be found to not be able to resume their original shapes because of a lack of plastic flow. By the apparatus of the present invention, the flexibility and deformability of red blood cells can be studied.

Figure 17A:
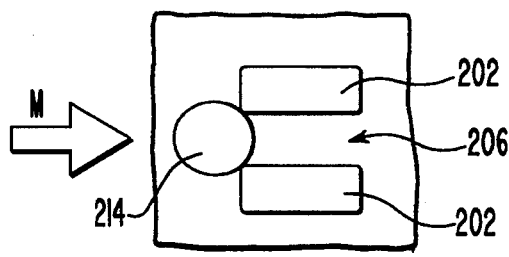
FIGS. 17A–17E illustrate in detail the movement of a healthy round cell between two adjacent obstacles of the type illustrated in FIGS. 15 and 16.
Figure 17B:
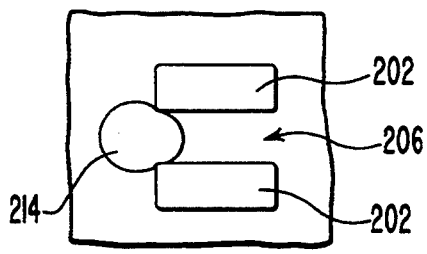
Figure 17C:
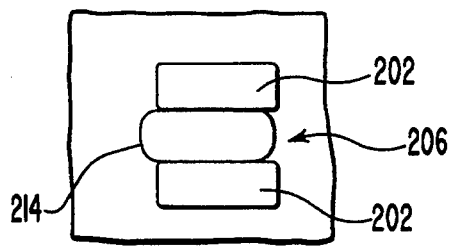
Figure 17D:
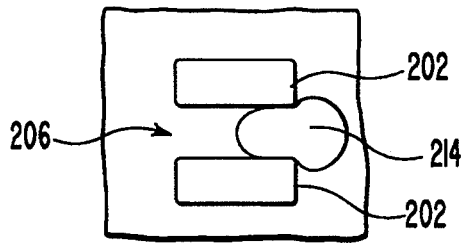
Figure 17E:
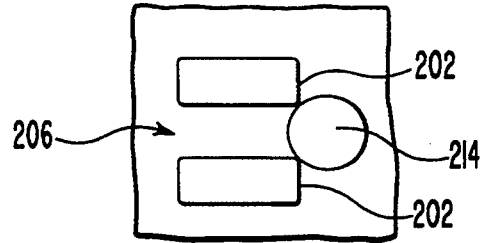

FIGS. 17A–17E illustrates an individual cell 214 moving through a pair of bunkers 202. As shown in FIG. 17A, before passing through bunkers 202, the cell 214 is perfectly disc shaped. In FIG. 17B, cell 214 is seen beginning to deform in order to fit between bunkers 202 in channel 206. FIG. 17C illustrates cell 214 deformed into an elongated thin shape to fit within channel 206. As shown in FIG. 17D, as cell 214 begins to move out of channel 206, cell 214 begins to regain its original disc shape. Once completely out of channel 206, as shown in FIG. 17E, the elasticity of cell 214 allows cell 214 to completely regain its original disc shape.

Figure 18A:
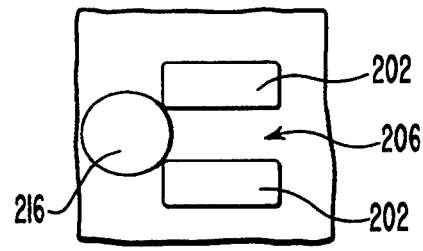
FIGS. 18A–18B illustrate in detail the movement of an unhealthy cell unable to deform and pass through the restriction formed by two adjacent obstacles of the type illustrated in FIGS. 15 and 16.
Figure 18B:
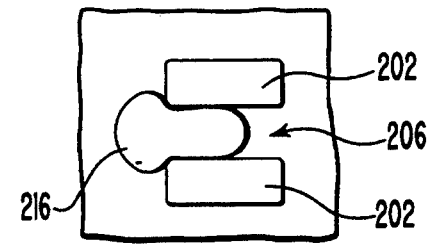

In contrast, FIGS. 18A–18B illustrate an unhealthy cell 216 whose elastic properties have been lost. Although unhealthy cell 216 has an original round disc shape of a healthy cell, its flexibility is diminished such that it cannot deform to fit into channel 206. As cell 216 passes through channel 206, cell 216 cannot deform into a thin elongated shape to fit into channel 206 and becomes stuck in the opening of channel 206. In the case of cancer cells, it is thought that where the cancer cells become stuck, a new tumor is grown. The activity of cancer cells can be studied with the teachings of the present invention.

Thus, it can be seen that by using the apparatus of the present invention, the elasticity and flexibility of cells can be studied. Further, the consequences of lack of plastic flow of the cells can be observed and studied. Further, still, the amount of energy consumed by the cell to deform and regain its shape can easily be measured and recorded.

Another important advantage and use of the present invention is to study and observe the physical properties of cells in a variety of chemical environments. Array 200 can be exposed to various chemical environments, such as irradiation, light illumination, or sickling phenomena imitations, before allowing the cells to migrate through array 200. The reactions of cells as they migrate through these various environments can then be studied. For example, experiments can be designed to determine what kinds of chemical reactions cause aging of the cells and destroy ability of cells to be flexible. Other experiments can be designed and conducted to determine the chemical effects on cancer cells. Ultimately, an unlimited number of cellular effects can be observed.

Also advantageous, the experiments can be easily repeated to verify data or to make minor changes to the experimental controls. Thus, cells can be sorted by desired physical properties, that is, by their reactions to various environments. As the cells are sorted, they can be separated and collected.

Another important advantage of the present invention with regard to studying cells is the reproducibility and repeatability of the array of obstacles. Since the arrays 200 can consist of obstacles which are repeated thousands of times, even subtle variations in small quantities in the membrane of the cell can be amplified. Additionally, by the apparatus of the present invention, many individual cells can be observed at once as they migrate through the channels 206 of the apparatus. Observation of more than just one cell is possible.

With regard to mobility of the cells through the apparatus of the present invention, cells can be migrated through array 200 using various fields. For example, migration can be caused by flowing fluid through the array in a hydrodynamic field through flow cytometry wherein water pressure is used to force the cells through the array. The cells may also be induced to move by a gravity field. Alternatively, magnetic beads may be placed on the apparatus to create a magnetic field to induce movement of the cells. Further, focused beams of light referred to as optical tweezers may be used to move the cells through array 200. Other means for inducing the cells to migrate through the array 200 are also within the scope of the present invention.

As one example of an embodiment within the scope of the present invention, the apparatus can be designed to simulate capillaries in the human body by having channeling means positioned within receptacle 24 which mimic the openings that the blood cell must pass through in the body. By precise control of chemical environment, channel opening and topology, flow velocity, and the application of theories of membrane physics, understanding can be obtained of how cells pass through complex environments, cell aging, and how the chemical environment of the cell solution controls the membrane properties.

The invention may be embodied in other specific forms without departing from its spirit other essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An electrophoresis device for sorting microstructures, such as cells, viruses, macromolecules, or minute particles in a fluid medium, said electrophoresis device comprising:

a. a substrate having a shallow receptacle located on a side thereof, said receptacle having first and second ends and a floor bounded on opposite sides by a pair of upstanding opposed side walls extending between said first and second ends of said receptacle, migration of the microstructures from the first end of said receptacle to said second end of said receptacle defining a migration direction for said receptacle the height of said side walls as measured normal to said floor of said receptacle defining a depth of said receptacle, said depth of said receptacle being commensurate with the size of the microstructures in the fluid medium, whereby when the microstructures are caused to migrate in the fluid medium from said first end of said receptacle to said second end of said receptacle, the microstructures do so in essentially a single layer; and b. sifting means positioned within said receptacle intermediate said first and second ends thereof traversing said migration direction for interacting with the microstructures to partially hinder the migration of the microstructures in said migration direction in the fluid medium;

c. ceiling means positioned over said sifting means for covering said receptacle and for causing migration of the microstructures within said receptacle to occur in essentially a single layer through said sifting means exclusively; and d. electric force means for generating an electric field in the fluid medium in said receptacle.

2. An electrophoresis device as recited in claim 1, wherein said ceiling means is so secured to said sifting means as to preclude migration of the microstructures between said sifting means and said ceiling means.

3. An electrophoresis device as recited in claim 1, wherein said sifting means comprises an array of obstacles upstanding from said floor of said receptacle, each of said obstacles having a top at the end thereof opposite from said floor of said receptacle.

4. An electrophoresis device as recited in claim 3, wherein the top of each of said obstacles is bonded to said ceiling means.

5. An electrophoresis device as recited in claim 3, wherein said obstacles of said array are arranged in a predetermined and reproducible pattern, each obstacle in said array of obstacles having a height measured in a direction normal to said floor of said receptacle, a length measured in a direction parallel to said migration direction, and a width measured in a direction normal to said migration direction, and wherein the distance of each of said obstacles from an adjacent of said obstacles defines a separation distance therebetween.

6. An electrophoresis device as recited in claim 5, wherein said height of each of said obstacles is in a range of from about 0.01 microns to about 20.0 microns.

7. An electrophoresis device as recited in claim 5, wherein said height of each of said obstacles is in a range of from about 0.01 microns to about 0.50 microns.

8. An electrophoresis device as recited in claim 5, wherein said height of each of said obstacles is in a range of from about 1.0 micron to about 5.0 microns.

9. An electrophoresis device as recited in claim 5, wherein said separation distance is substantially equal to a radius of gyration of each of the microstructures.

10. An electrophoresis device as recited in claim 5, wherein said separation distance is in a range of from about 0.01 microns to about 50.0 microns.

11. An electrophoresis device as recited in claim 5, wherein said separation distance is in a range of from about 0.01 microns to about 1.0 micron.

12. An electrophoresis device as recited in claim 5, wherein said separation distance is in a range of from about 1.0 micron to about 20.0 microns.

13. An electrophoresis device as recited in claim 5, wherein said separation distance is substantially equal to said length of said obstacles.

14. An electrophoresis device as recited in claim 5, wherein said obstacles comprise posts.

15. An electrophoresis device as recited in claim 5, wherein said obstacles have a v-shaped cross section in a plane disposed parallel to said floor of said receptacle, said v-shaped cross section of said obstacles comprising first and second arms intersecting at an end of each to form a vertex of said v-shaped cross section, the other ends of said first and second arms remote from said vertex forming an open end of said v-shaped cross section.

16. An electrophoresis device as recited in claim 15, wherein the open end of said v-shaped cross section of said obstacles is disposed opposing said migration direction of said receptacle.

17. An electrophoresis device as recited in claim 5, wherein said obstacles have a cup-shaped cross section in a plane disposed parallel to said floor of said receptacle, said cup-shaped cross section of said obstacles comprising:
   a. a first leg and a second leg positioned in opposed relationship substantially parallel to said migration direction, each of said first and second legs having thereby oppositely disposed first and second ends; and
   b. a third leg positioned substantially perpendicular to said migration direction and being connected between said first ends of each of said first and second legs, thereby to define between said second ends of said first and second legs an open end of said cup-shaped cross section.

18. An electrophoresis device as recited in claim 17, wherein said open end of said cup-shaped cross section of said obstacles is disposed opposing said migration direction of said receptacle.

19. An electrophoresis device as recited in claim 5, wherein said height of said obstacles is substantially equal to said depth of said receptacle.

20. An electrophoresis device as recited in claim 3, wherein the top of each of said obstacles is ion fusion bonded to said ceiling means.

21. An electrophoresis device as recited in claim 1, wherein said electric field generated by said electric force means is so polarized as to induce the microstructures to migrate through the fluid medium from said first end of said receptacle to said second end of said receptacle.

22. An electrophoresis device as recited in claim 1, wherein said electric force means comprises:
   a) a first electrode positioned at said first end of said receptacle; and
   b) a second electrode positioned at said second end of said receptacle.

23. An electrophoresis device as recited in claim 22, wherein said first and second electrodes each comprise a metal strip disposed on said floor of said receptacle.

24. An electrophoresis device as recited in claim 22, wherein said electric force means further comprises a power source having a negative and a positive pole, said power source being coupled between said first and said second electrodes.

25. An electrophoresis device as recited in claim 24, wherein said negative pole of said power source is coupled to said first electrode, thereby to induce negatively charged microstructures to migrate through said receptacle in said migration direction.

26. An electrophoresis device as recited in claim 24, wherein said positive pole of said power source is coupled to said first electrode, thereby to induce positively charged microstructures to migrate through said receptacle in said migration direction.

27. An electrophoresis device as recited in claim 1, wherein said electric field is non-alternating.

28. An electrophoresis device as recited in claim 1, wherein said electric field has an intensity in a range from about 0.1 volts per centimeter to about 20 volts per centimeter.

29. An electrophoresis device as recited in claim 1, wherein said electric field has an intensity of about 1.0 volt per centimeter.

30. An electrophoresis device as recited in claim 1, wherein said ceiling means comprises a coverslip extending across said receptacle from one of said pair of upstanding opposing side walls to the other.

31. An electrophoresis device as recited in claim 30, wherein said coverslip and said substrate are comprised of materials having substantially similar coefficients of thermal expansion.

32. An electrophoresis device as recited in claim 30, wherein said coverslip is comprised of quartz.

33. An electrophoresis device as recited in claim 30, wherein said coverslip is comprised of sapphire.

34. An electrophoresis device as recited in claim 30, wherein said coverslip is comprised of pyrex.

35. An electrophoresis device as recited in claim 30, wherein said coverslip is comprised of silicon.

36. An electrophoresis device as recited in claim 30, wherein said coverslip is transparent.

37. An electrophoresis device as recited in claim 30, wherein said cover slip is ion fusion bonded to said pair of upstanding opposing side walls.

38. An electrophoresis device as recited in claim 1, wherein said ceiling means is comprised of a ceramic.

39. An electrophoresis device as recited in claim 1, wherein said substrate is comprised of a material that can be subjected to photolithographic etching.

40. An electrophoresis device as recited in claim 1, wherein said substrate is comprised of silicon.

41. An electrophoresis device as recited in claim 1, wherein said substrate is comprised of quartz.

42. An electrophoresis device as recited in claim 1, wherein said substrate is comprised of sapphire.

43. An electrophoresis device as recited in claim 1, wherein said substrate and said sifting means are integrally formed.

44. An electrophoresis device as recited in claim 1, wherein said substrate and said sifting means are comprised of a material that can be subjected to photolithographic etching.

45. An electrophoresis device as recited in claim 1, wherein said substrate and said sifting means are comprised of silicon.

46. An electrophoresis device for fractionating microstructures, such as free cells, viruses, macromolecules, or minute particles in a fluid medium, said apparatus comprising:

a. a substrate having a shallow receptacle located on a side thereof, said receptacle having first and second ends and a floor bounded on opposite sides by a pair of upstanding opposed side walls extending between said first and second ends of said receptacle, the height of said side walls defining a depth of said receptacle, said depth of said receptacle being commensurate with the size of the microstructures in the fluid medium, whereby when the microstructures are caused to migrate in the fluid medium from said first end to said second end of said receptacle, the microstructures do so in essentially a single layer;

b. an array of obstacles upstanding from said floor of said receptacle intermediate said first and second ends thereof, each of said obstacles of said array being positioned within said array in a predetermined reproducible pattern; and c. a coverslip extending across said receptacle from one of said pair of upstanding opposing side walls to the other, said coverslip having substantially the same coefficient of thermal expansion as said substrate, and said coverslip being secured to the end of each of said obstacles remote from said floor; and d. electric force means for generating an electric field in the fluid medium in said receptacle, thereby to induce electrically charged microstructures to migrate through the fluid medium.

47. An apparatus as recited in claim 46, wherein said obstacles are integrally formed with said substrate.

48. An apparatus as recited in claim 46, wherein said substrate, said coverslip, and said obstacles are comprised of materials having substantially similar coefficients of thermal expansion.

49. An apparatus as recited in claim 46, wherein said obstacles are integrally formed at one end thereof with said substrate and bonded at the other end thereof to said coverslip.

50. An apparatus as recited in claim 46, wherein the space between adjacent of said obstacles in a cross section of said array taken normal to said floor of said receptacle defines pores of a lattice structure for sorting the microstructures, and said pores of said lattice structure assume a generally rectangular shape.

51. An apparatus as recited in claim 46, further comprising sensor means for detecting the intensity of said electric field generated within said array of obstacles between predetermined first and second points therein.

52. An apparatus as recited in claim 51, wherein said sensor means is electrically coupled with said electric force to vary the intensity of said electric field in a predetermined manner.

53. An apparatus as recited in claim 51, wherein said sensor means comprises:

a. a first sensor electrode positioned within said array at said first predetermined point; and b. a second sensor electrode positioned within said array at said second predetermined point.

54. An apparatus as recited in claim 53, wherein said first and second sensor electrodes comprise metal strips disposed on said floor of said receptacle among said obstacles of said array.

55. An apparatus as recited in claim 53, wherein said sensor means further comprises control means coupled to said first and second sensor electrodes for maintaining said electric field in said array at a predetermined intensity.

56. An apparatus as recited in claim 55, wherein said control means comprises:

a. a differential amplifier circuit having first and second input terminals coupled, respectively, to said first and second sensor electrodes, said differential amplifier circuit producing an output signal corresponding to the intensity of said electric field in said array between said first and second sensor electrodes;

b. a comparator means coupled to said differential amplifier circuit for producing a control signal reflecting the difference between said output signal of said differential amplifier and a reference voltage reflecting said predetermined intensity of said electric field in said array; and c. driver means coupled to said comparator means for varying the output of said electric force means to increase the intensity of said electric field in said array when said control signal corresponds to an output signal from said differential amplifier means that is less than said reference voltage, and to decrease the intensity from said electric field in said array when said control signal corresponds to an output signal from said differential amplifier that is greater than said predetermined reference voltage.

57. An apparatus as recited in claim 56, wherein said control means further comprises:

a. a first amplifier circuit coupled between said first sensor electrode and said first input terminal of said differential amplifier circuit; and b. a second amplifier circuit coupled between said second sensor electrode and said second input terminal of said differential amplifier.

58. An apparatus as recited in claim 56, wherein said reference voltage is selectively variable.

59. An apparatus as recited in claim 46, wherein said coverslip affords visual observation of the migration of the microstructures.

60. An apparatus as recited in claim 59, wherein said cover slip is transparent.

61. An electrophoresis device as recited in claim 46, wherein said coverslip is transparent.

62. An electrophoresis device as recited in claim 46, wherein each of said obstacles in said array has a top at the end thereof opposite from said floor of said receptacle, and said cover slip is ion fusion bonded to said pair of upstanding opposing side walls and to said top of each of said obstacles in said array.

63. A method for electrophoretically sorting microstructures, such as free cells, viruses, macromolecules, or minute particles, comprising the steps of:

a. placing the microstructures in a fluid medium;

b. introducing the fluid medium with the microstructures therein into a receptacle having a first end and a second end and a floor bounded by a pair of upstanding opposing side walls and having an array of upstanding obstacles in a predetermined and reproducible pattern positioned between said first and second ends thereof, the height of said side walls defining a depth of said receptacle, said depth of said receptacle being commensurate with the size of the microstructures in the fluid medium, thereby to cause migration of the microstructures in the fluid medium within said receptacle to occur in essentially a single layer through said array of obstacles; and c. generating an electric field in the fluid medium between said first and second ends of said receptacle.

64. A method a recited in claim 63, wherein a first electrode is positioned on said floor at said first end of said receptacle and a second electrode is positioned on said floor at said second end of said receptacle, and said step of generating comprises the step of coupling a power source having a negative and a positive poles between said first and second electrodes, thereby to so polarize said electric field between said first and second ends of said receptacle as to induce the microstructures to migrate through said fluid medium from said first end of said receptacle to said second end of said receptacle.

65. A method as recited in claim 64, wherein said positive pole of said power source is coupled to said first electrode, thereby to induce positively charged microstructures to migrate through said receptacle from said first end to said second end thereof.

66. A method as recited in claim 64, wherein said negative pole of said power source is coupled to said first electrode, thereby to induce negatively charged microstructures to migrate through said receptacle from said first end to said second end thereof.

67. A method as recited in claim 63, wherein said electric field is non-alternating.

68. A method as recited is claim 63, wherein said electric field has an intensity in a range from about 0.1 volts per centimeter to about 20.0 volts per centimeter.

69. A method as recited in claim 63, wherein said electric field has an intensity of about 1.0 volt per centimeter.

70. A method as recited in claim 63, further comprising the step of detecting the intensity of said electric field in said array of obstacles between predetermined first and second points therein.

71. A method as recited in claim 70, wherein said method further comprises the step of utilizing the intensity of said electric field said predetermined first and second points in said array of obstacles from said step of detecting for maintaining said electric field in said array at a predetermined intensity.

72. A method as recited in claim 71, wherein a first sensor electrode is positioned within an array of obstacles at a first predetermined point and a second sensor electrode is positioned within said array of obstacles at said second predetermined point, and wherein said step of maintaining said electric field in said array at a predetermined intensity comprises the steps of:
 a. producing between said first and second sensor electrodes an output signal corresponding to the intensity of said electric field in said array of obstacles;
 b. producing a control signal reflecting the difference between said output signal and a reference voltage reflecting said predetermined intensity of said electric field in said array of obstacles; and
 c. varying the intensity of said electric field in said array of obstacles to increase said intensity when said control signal corresponds to an output signal that is less than said reference voltage, and to decrease said intensity when said control signal corresponds to an output signal that is greater than said reference voltage.

73. A method as recited in claim 72, wherein said step of utilizing further comprises the steps of:
 a. amplifying the signal at said first sensor electrode; and
 b. amplifying the signal received at said second sensory electrode.

74. A method as recited in claim 72, further comprising the step of varying said reference voltage.

75. A method as recited in claim 63, further comprising the step of visually observing migration of the microstructures through said array of obstacles.

* * * * *

UNITED STATES PATENT AND TRADEMARK OFFICE
CERTIFICATE OF CORRECTION

PATENT NO. : 5,427,663
DATED : June 27, 1995
INVENTOR(S) : ROBERT H. AUSTIN et al.

It is certified that error appears in the above-indentified patent and that said Letters Patent is hereby corrected as shown below:

Column 6, line 62, "bounded" should be --bound--
    Column 9, line 45, "is preferred," should be --is preferred;--
    Column 9, line 46, after "sapphire" insert --,--
    Column 13, line 22, "there between" should be --therebetween--
    Column 22, line 35, "FIGS. 17A-17E illustrates" should be --FIGS. 17A-17E illustrate--

Column 29, line 9, "a positive poles" should be --a positive pole--
    Column 30, line 1, after "field" insert --said--

Signed and Sealed this

Twenty-sixth Day of March, 1996

*Attest:*

BRUCE LEHMAN

*Attesting Officer*    *Commissioner of Patents and Trademarks*